(12) United States Patent
Lee et al.

(10) Patent No.: US 10,908,163 B2
(45) Date of Patent: Feb. 2, 2021

(54) ANALYSIS METHOD OF MOLECULAR INTERACTIONS ON PROTEIN NANOPARTICLES USING FLOW CYTOMETRY

(71) Applicant: Korea Research Institute of Bioscience and Biotechnology, Daejeon (KR)

(72) Inventors: Seung-Goo Lee, Daejeon (KR); Yu Jung Kim, Daejeon (KR); Jongsik Gam, Daejeon (KR); Haseong Kim, Daejeon (KR); Dae-Hee Lee, Daejeon (KR); Heung-Chae Jung, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 277 days.

(21) Appl. No.: 15/229,102

(22) Filed: Aug. 4, 2016

(65) Prior Publication Data
US 2017/0192009 A1 Jul. 6, 2017

Related U.S. Application Data

(63) Continuation-in-part of application No. PCT/KR2015/001226, filed on Feb. 6, 2015.

(30) Foreign Application Priority Data

Feb. 7, 2014 (KR) .................. 10-2014-0014334

(51) Int. Cl.
*G01N 33/68* (2006.01)
*G01N 33/58* (2006.01)

(52) U.S. Cl.
CPC ....... *G01N 33/6803* (2013.01); *G01N 33/582* (2013.01); *G01N 33/68* (2013.01)

(58) Field of Classification Search
None
See application file for complete search history.

(56) References Cited

U.S. PATENT DOCUMENTS

| | | | |
|---|---|---|---|
| 2006/0257887 A1 | 11/2006 | Waldo et al. | |
| 2008/0153111 A1 | 6/2008 | Nibert et al. | |
| 2009/0105089 A1 | 4/2009 | Renaut et al. | |
| 2013/0052660 A1 | 2/2013 | Lee et al. | |
| 2015/0044712 A1 | 2/2015 | Heo et al. | |

FOREIGN PATENT DOCUMENTS

| | | |
|---|---|---|
| JP | 2003-294736 A | 10/2003 |
| KR | 10-2012-0048545 A | 5/2012 |
| KR | 10-2013-0023057 A | 3/2013 |
| KR | 10-1356787 B1 | 2/2014 |
| WO | 2006/099486 A2 | 9/2006 |
| WO | 2013/048185 A2 | 4/2013 |

OTHER PUBLICATIONS

Bergmans et al, Journal of Bacteriology, May 1981, p. 564-570.*
Getz et al., 2012, Methods in Enzymology, vol. 503, pp. 75-97.*
Garcia-Fruitos et al, Microbial Cell Factories 2005, 4:27 pp. 1-6.*
Berdichevsky, Protein Expression and Puri®cation 17, 249-259 (1999).*
Helander et al., 2000, International Journal of Food Microbiology, vol. 60 pp. 153-161.*
Merrick et al., 1987, Journal of General Microbiology, vol. 133 pp. 2053-2057.*
Wolf, Nonconventional Yeast in Biotechnology, Springer, 1996, relevant pp. 369-370.*
Lee et al., PNAS, 2012, vol. 109 No. 9, pp. 3299-3304.*
Felix, "Permeabilized Cells," Analytical Biochemistry, 120: 211-234 (1982).
Choi et al., "Controlled Localization of Functionally Active Proteins to Inclusion Bodies Using Leucine Zippers," PLOS One, 9: e97093 (2014).
Extended European Search Report issued in corresponding European Patent Application No. 15746712.7 dated Aug. 31, 2017.
Inoue et al., "High efficiency transformation of *Escherichia coli* with plasmids," Gene, 96: 23-28 (1990).
Huang et al., "Active inclusion bodies of acid phosphatase PhoC: aggregation induced by GFP fusion and activities modulated by linker flexibility," Microbial Cell Factories, 12: 25 (2013).
Lin et al., "Screening and Selection Methods for Large-Scale Analysis of Protein Function," Angewandte Chemie International Edition, 41: 4402-4425 (2002).
Hanes et al., "In vitro selection and evolution of functional proteins by using ribosome display," Proceedings of the National Academy of Sciences, 94: 4937-4942 (1997).
Tawfik et al., "Man-made cell-like compartments for molecular evolution," Nature Biotechnology, 16: 652-656 (1998).
Smith et al., "Phage Display," Chemical Reviews, 97: 391-410 (1997).
Boder et al., "Yeast surface display for screening combinatorial polypeptide libraries," Nature Biotechnology, 15: 553-557 (1997).
Lee et al., "Small-Molecule-Based Nanoassemblies as Inducible Nanoprobes for Monitoring Dynamic Molecular Interactions Inside Live Cells," Angewandte Chemie International Edition, 50: 8709-8713 (2011).

(Continued)

*Primary Examiner* — Antonio Galisteo Gonzalez
(74) *Attorney, Agent, or Firm* — Morgan, Lewis & Bockius LLP

(57) ABSTRACT

The present invention relates to a method for analyzing the interaction between a binding protein and a target material, including measuring the interaction between the binding protein and a target material using an interaction trapper (IT) cell. The IT cell has the binding protein displayed on the surface of intracellular inclusion bodies, i.e., insoluble aggregates, by expressing a fusion protein which forms active protein particles containing the binding protein. The method includes increasing cell permeability without affecting the activity of the binding protein displayed on the cells and genetic information.

25 Claims, 24 Drawing Sheets
Specification includes a Sequence Listing.

(56) References Cited

OTHER PUBLICATIONS

Zhong, "Nanomaterials in fluorescence-based biosensing," Analytical and Bioanalytical Chemistry, 394: 47-59 (2009).
Nahalka et al., "Fusion to a Pull-Down Domain: A Novel Approach of Producing Trigonopsis variabilis D-Amino Acid Oxidase as Insoluble Enzyme Aggregates," Biotechnology and Bioengineering. 97: 454-461 (2007).
Garcia-Fruitos et al., "Aggregation as bacterial inclusion bodies does not imply inactivation of enzymes and fluorescent proteins," Microbial Cell Factories 4: 27 (2005).
International Search Report issued in related International Patent Application No. PCT/KR2015/001226 dated May 26, 2015.
Office Action issued in related European Patent Application No. 15746712.7 dated Dec. 5, 2018.

\* cited by examiner

[FIG. 1]
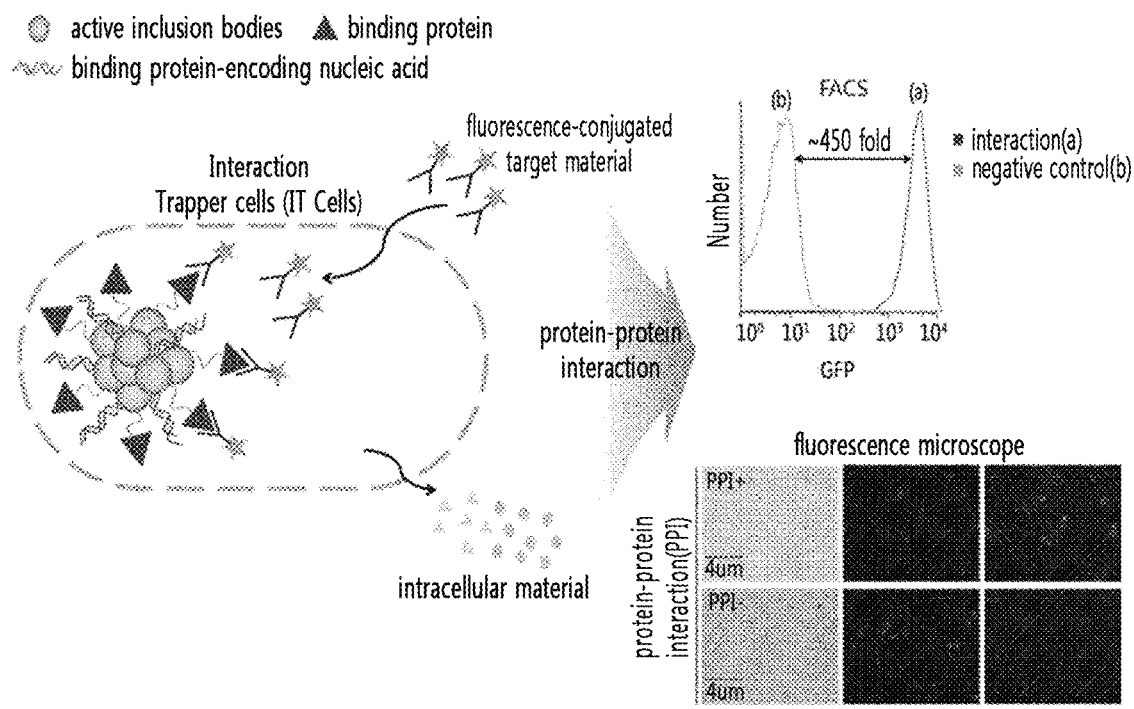

[FIG. 2]
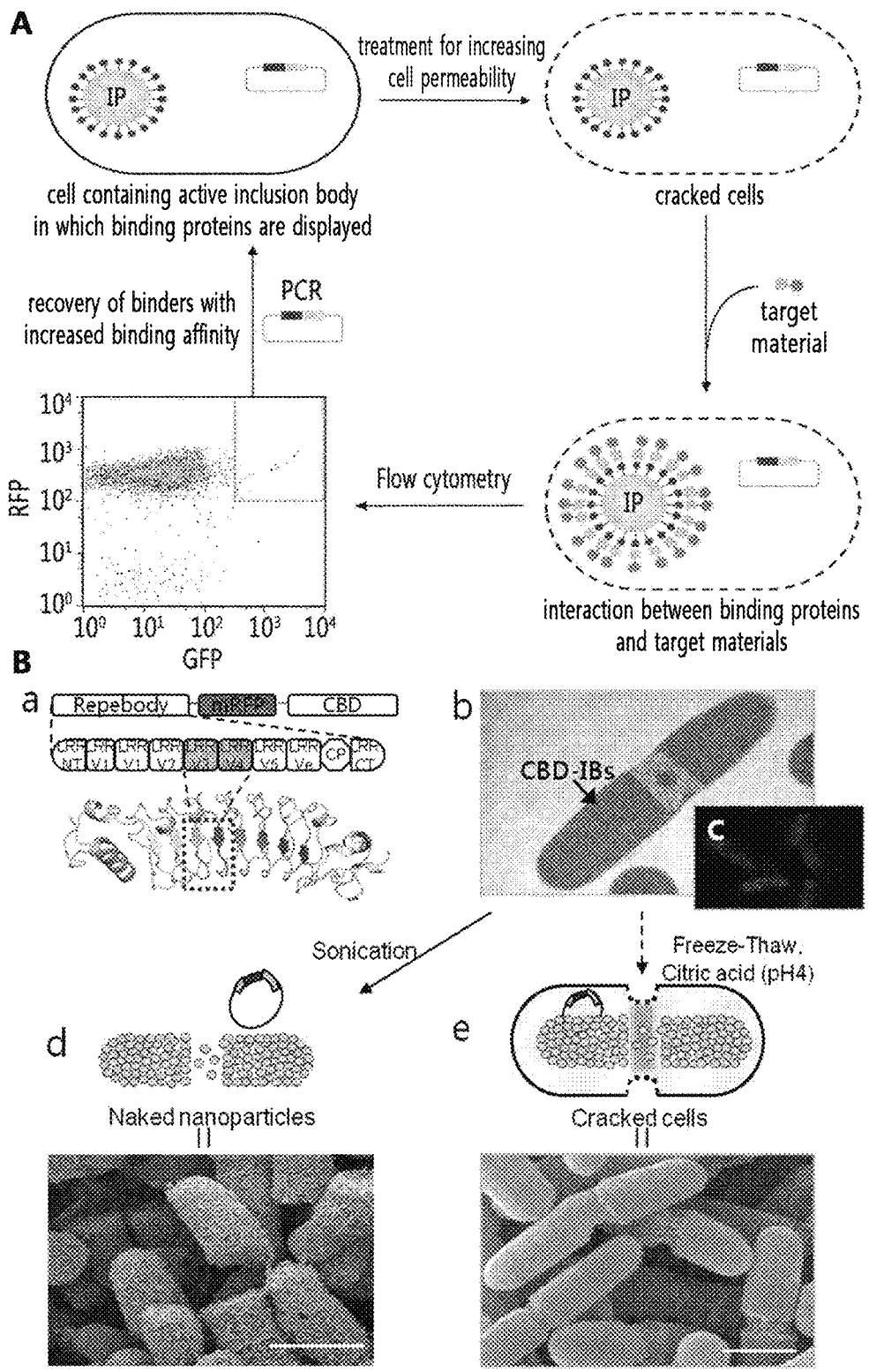

[FIG. 3]
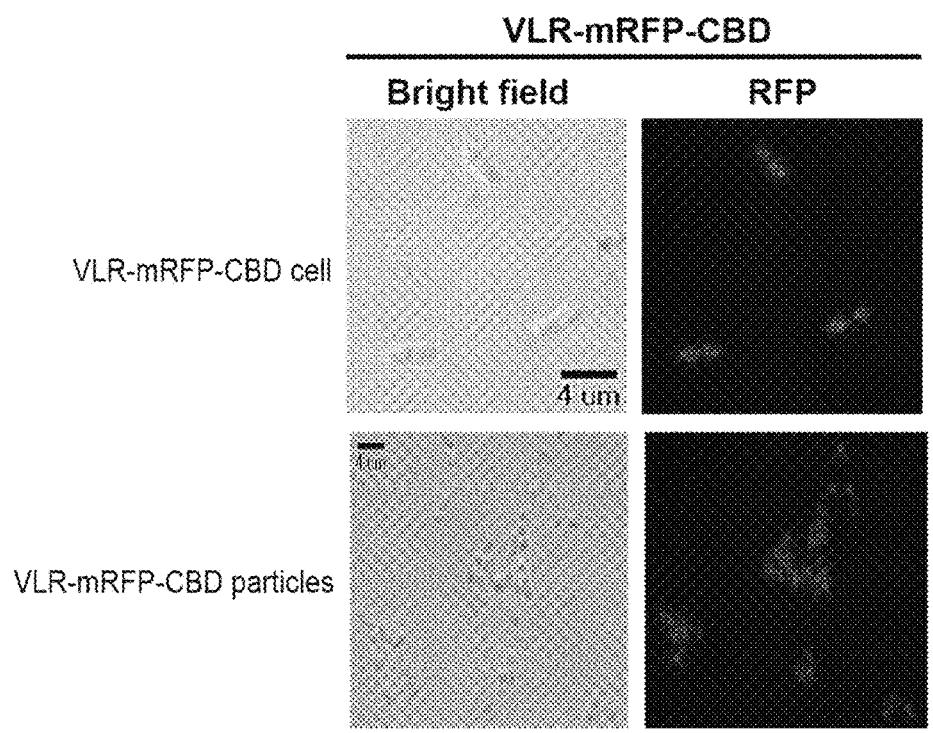

[FIG. 4]
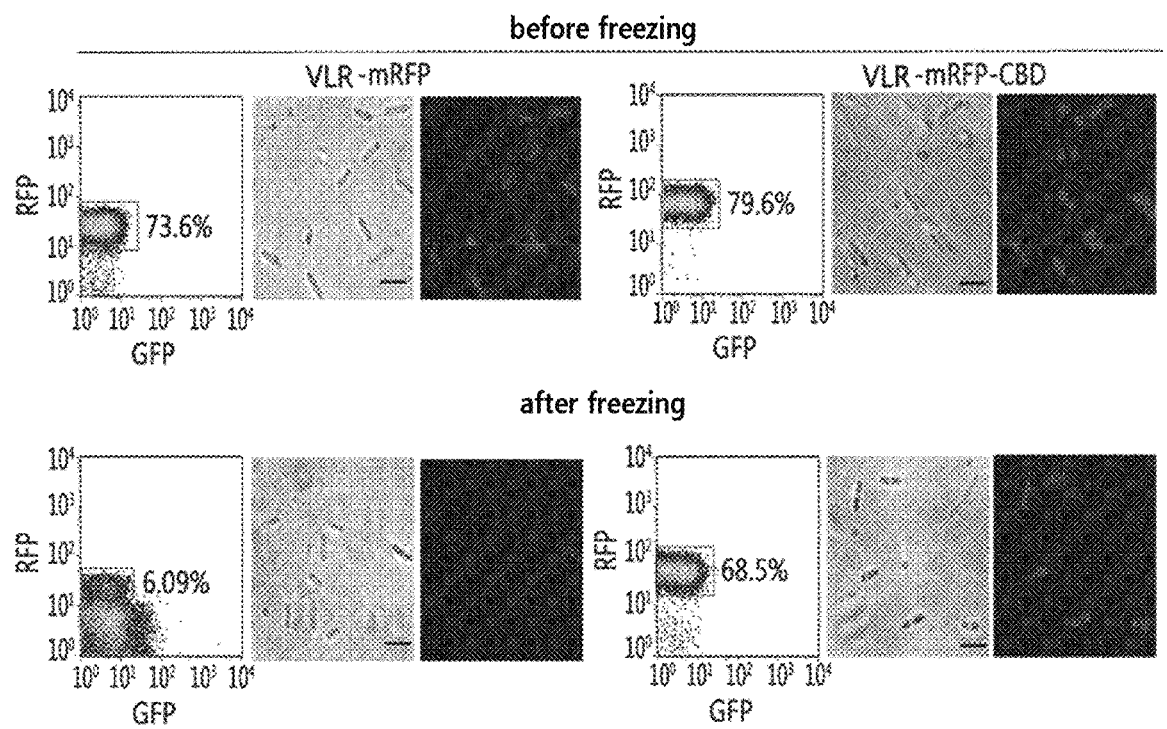

[FIG. 5]
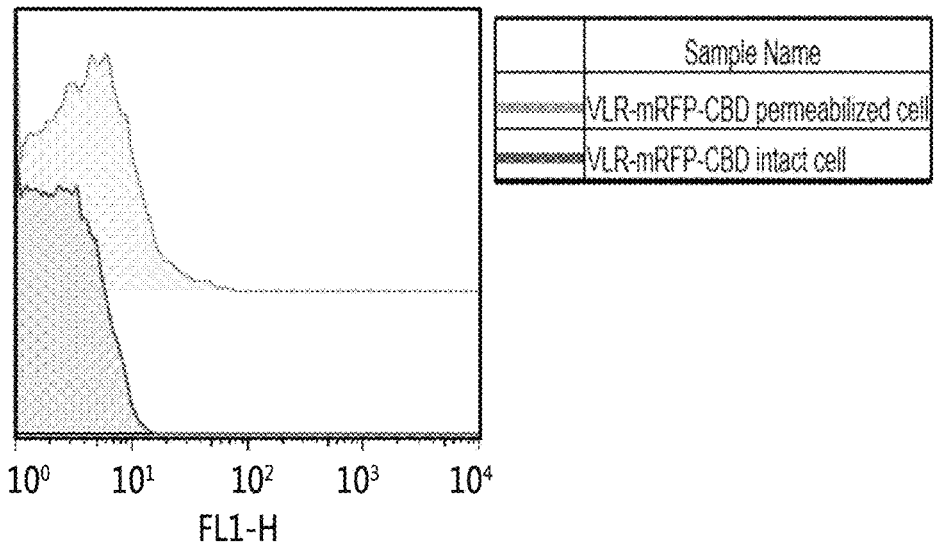
[FIG. 6]
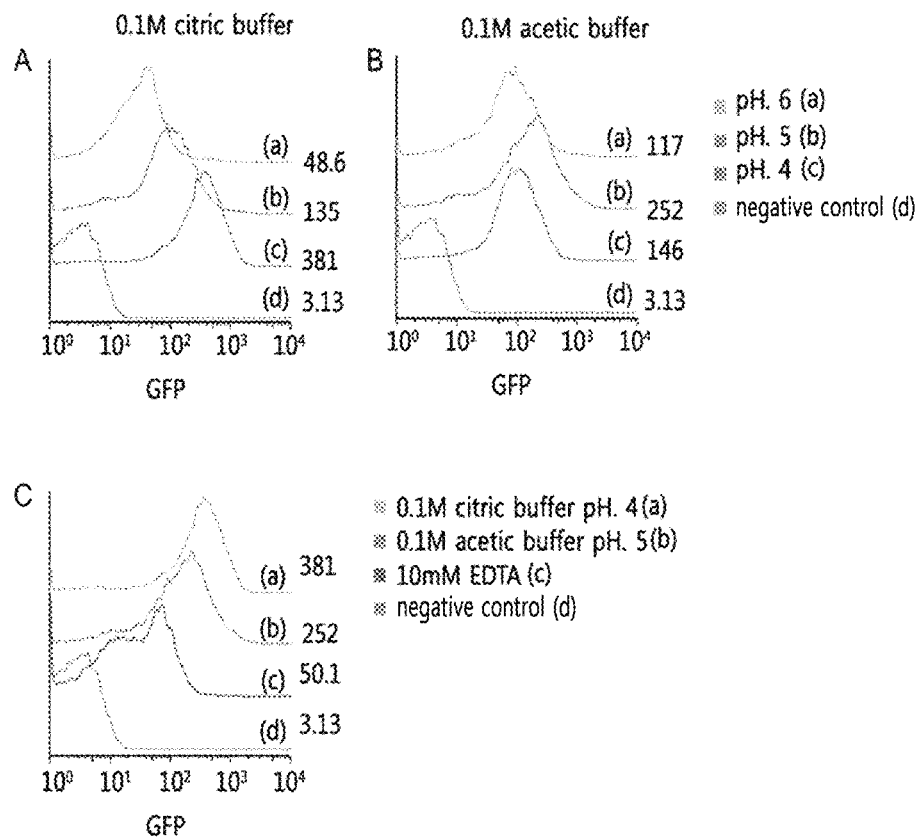

[FIG. 7]
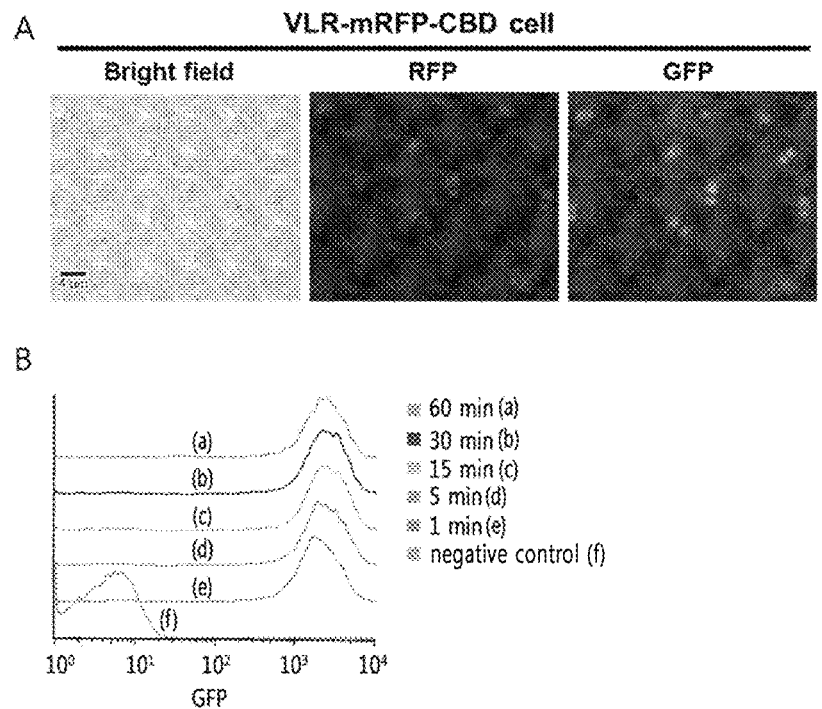
[FIG. 8]
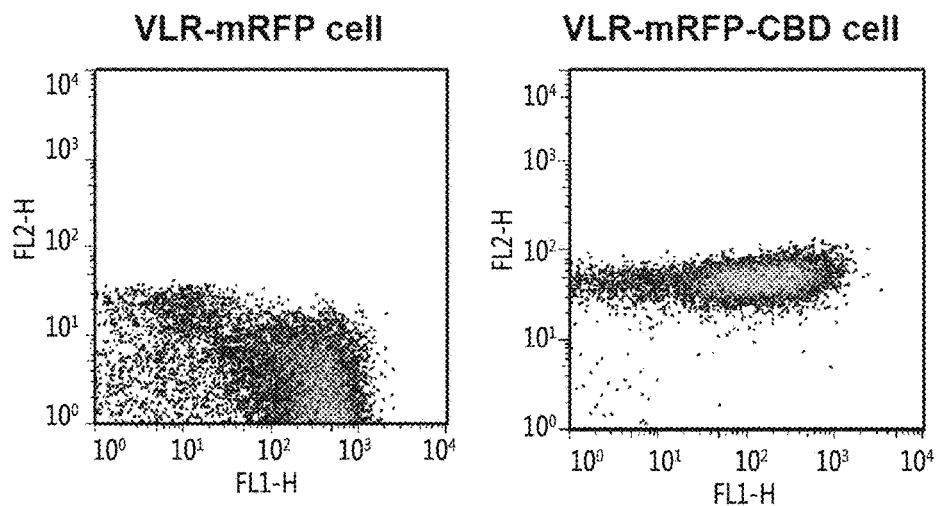

[FIG. 9]

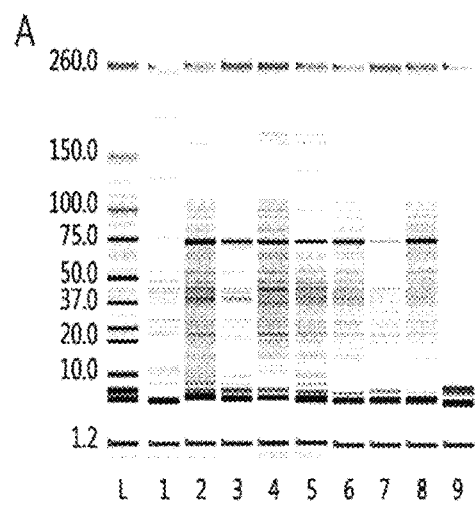 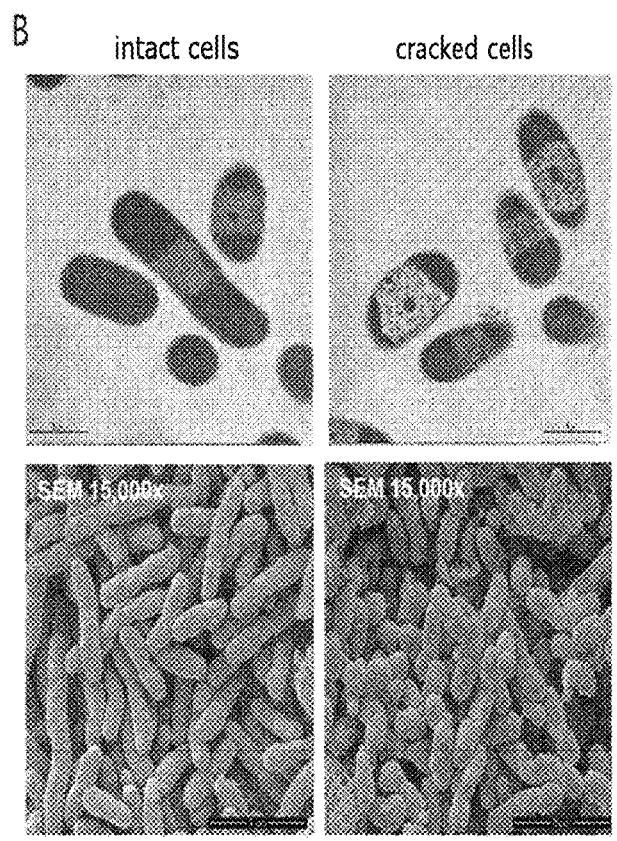

1. whole cells (negative control)
2. whole cells after ultrasonication (positive control)
3. precipitate of cells after ultrasonication (positive control)
4. supernatant of cells after ultrasonication
5. whole cells after freezing-thawing
6. precipitate of cells after freezing-thawing
7. supernatant of cells after freezing-thawing
8. precipitate of cells after freezing-thawing and acid solution treatment
9. supernatant of cells after freezing-thawing and acid solution treatment

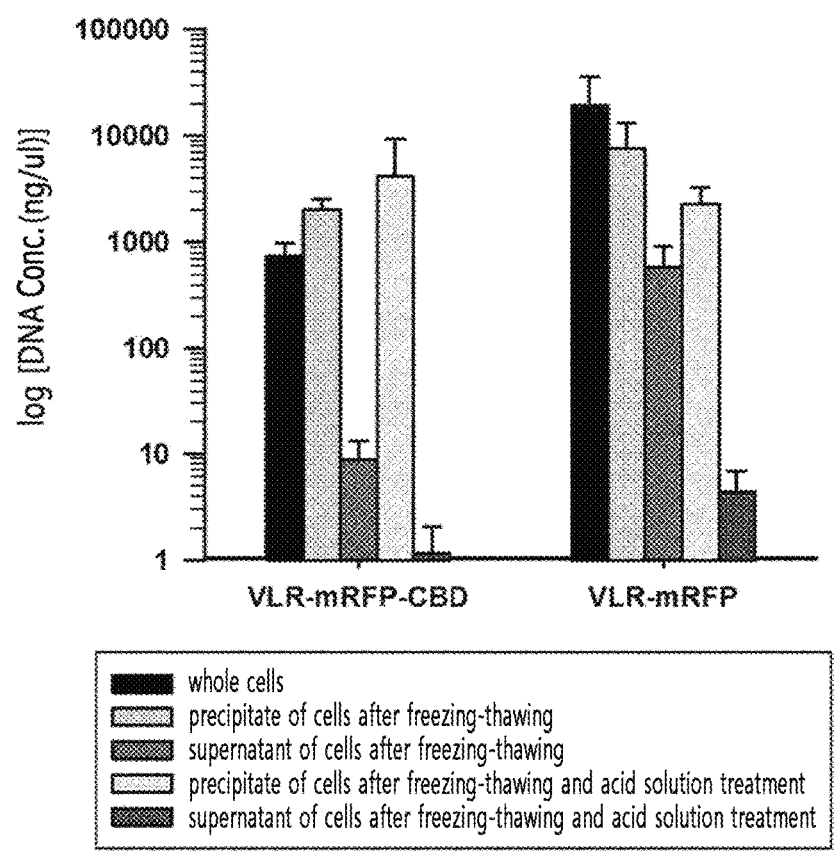
[FIG. 10]

[FIG. 11a]
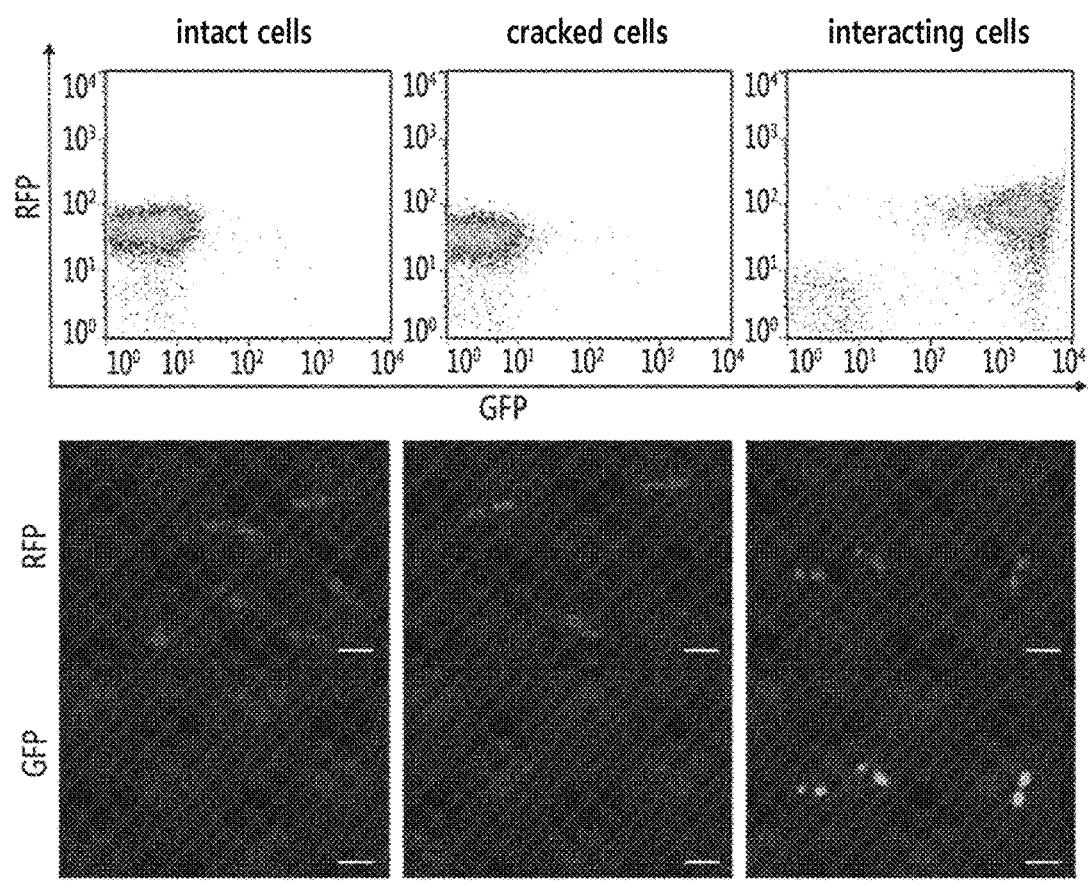

[FIG. 11b]
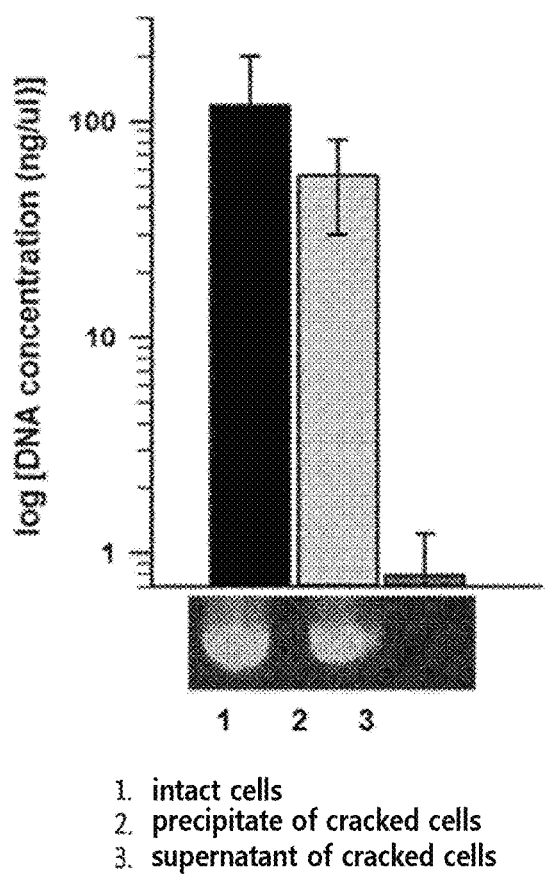
1. intact cells
2. precipitate of cracked cells
3. supernatant of cracked cells

[FIG. 11c]
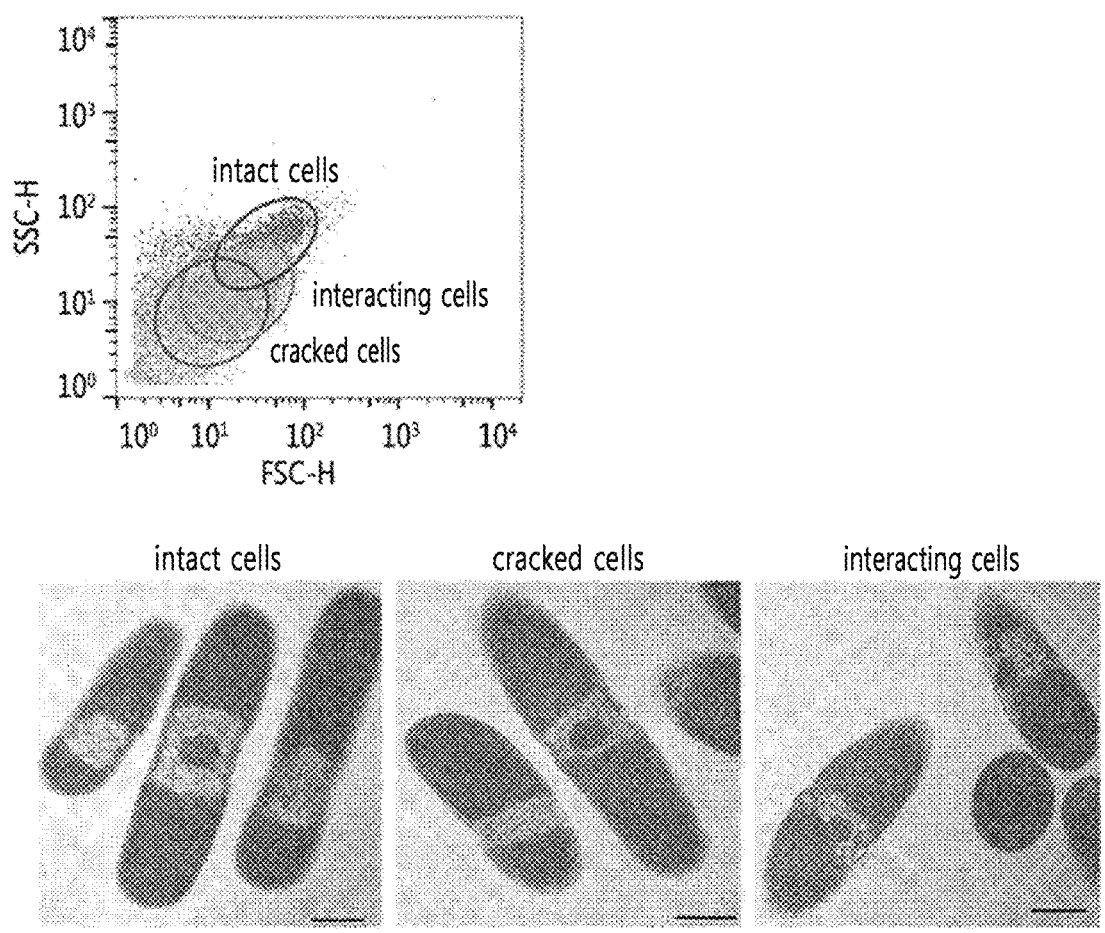

[FIG. 12]
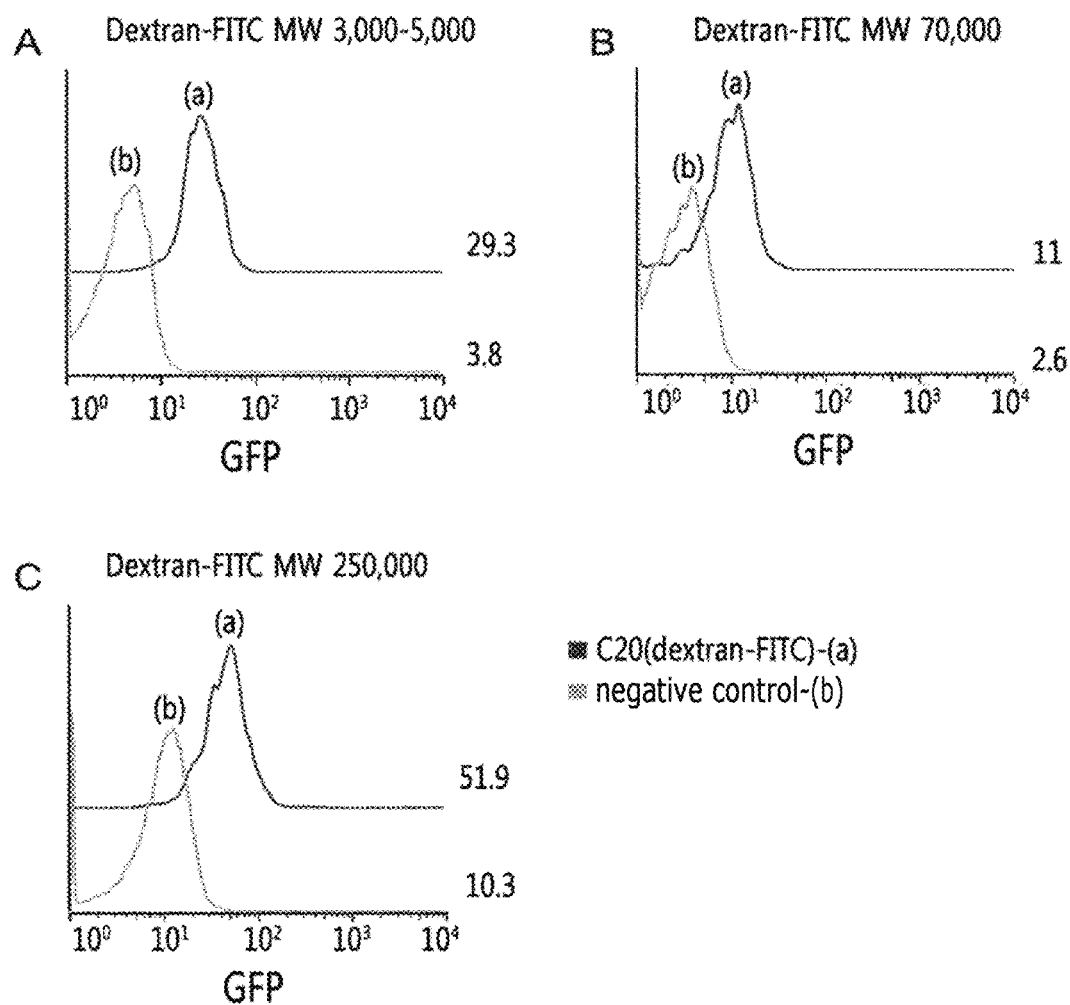

[FIG. 13]
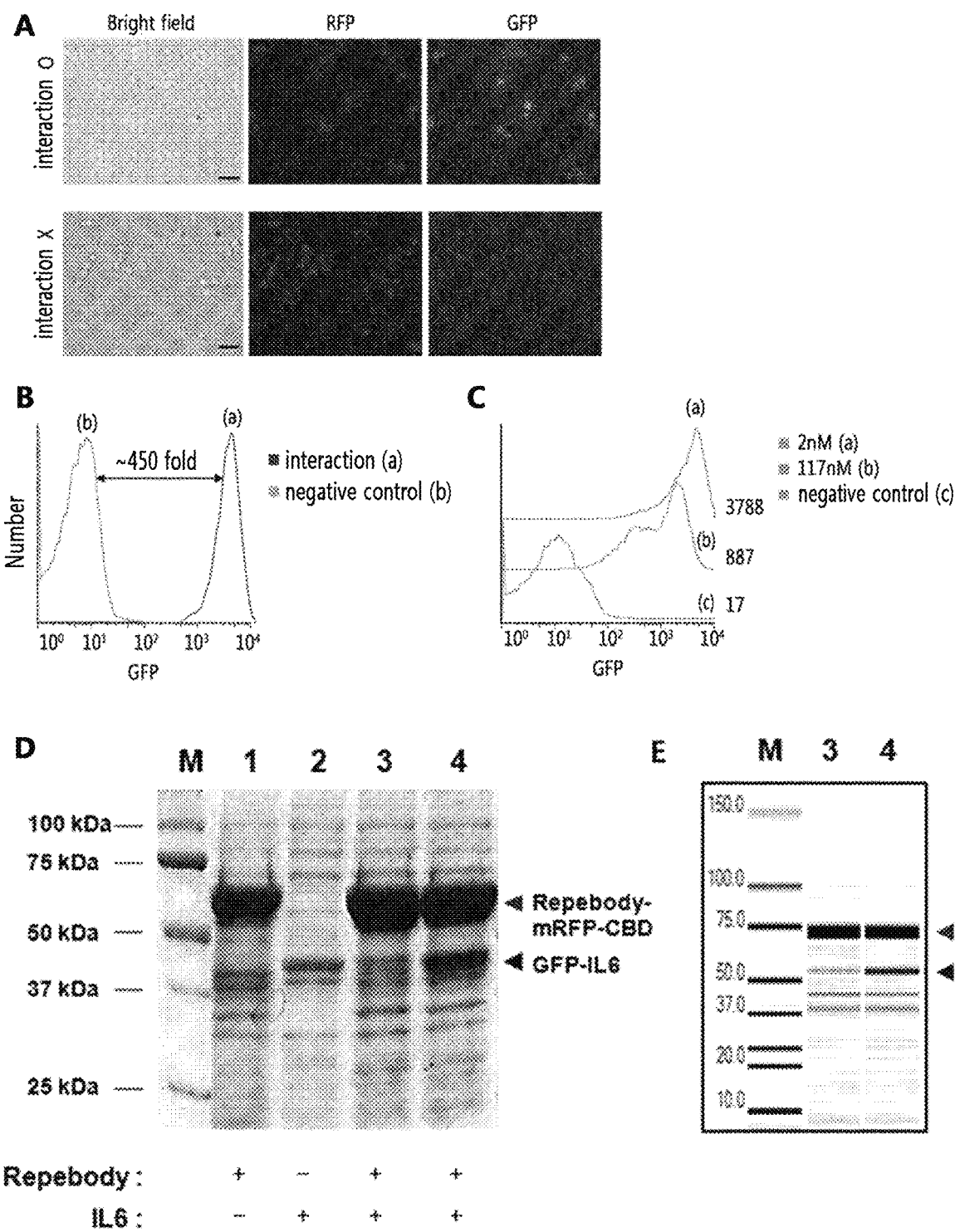

[FIG. 14]
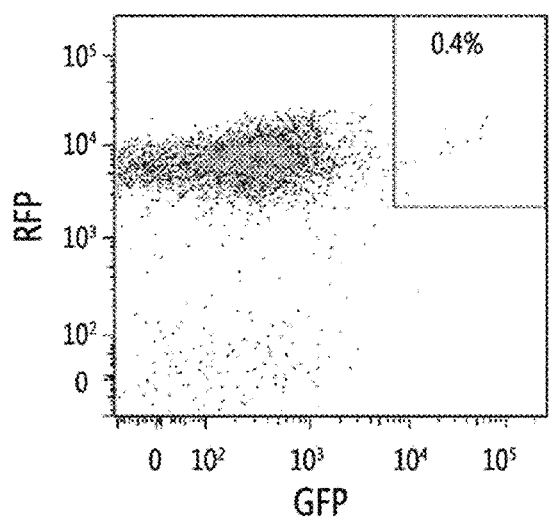
| clones | initial purity | recovered purity | screening efficiency |
|---|---|---|---|
| D3E8 | 0.01% | 333% | 33,300 |
| F11 | 0.1% | 3,100% | 31,000 |

[FIG. 15a]
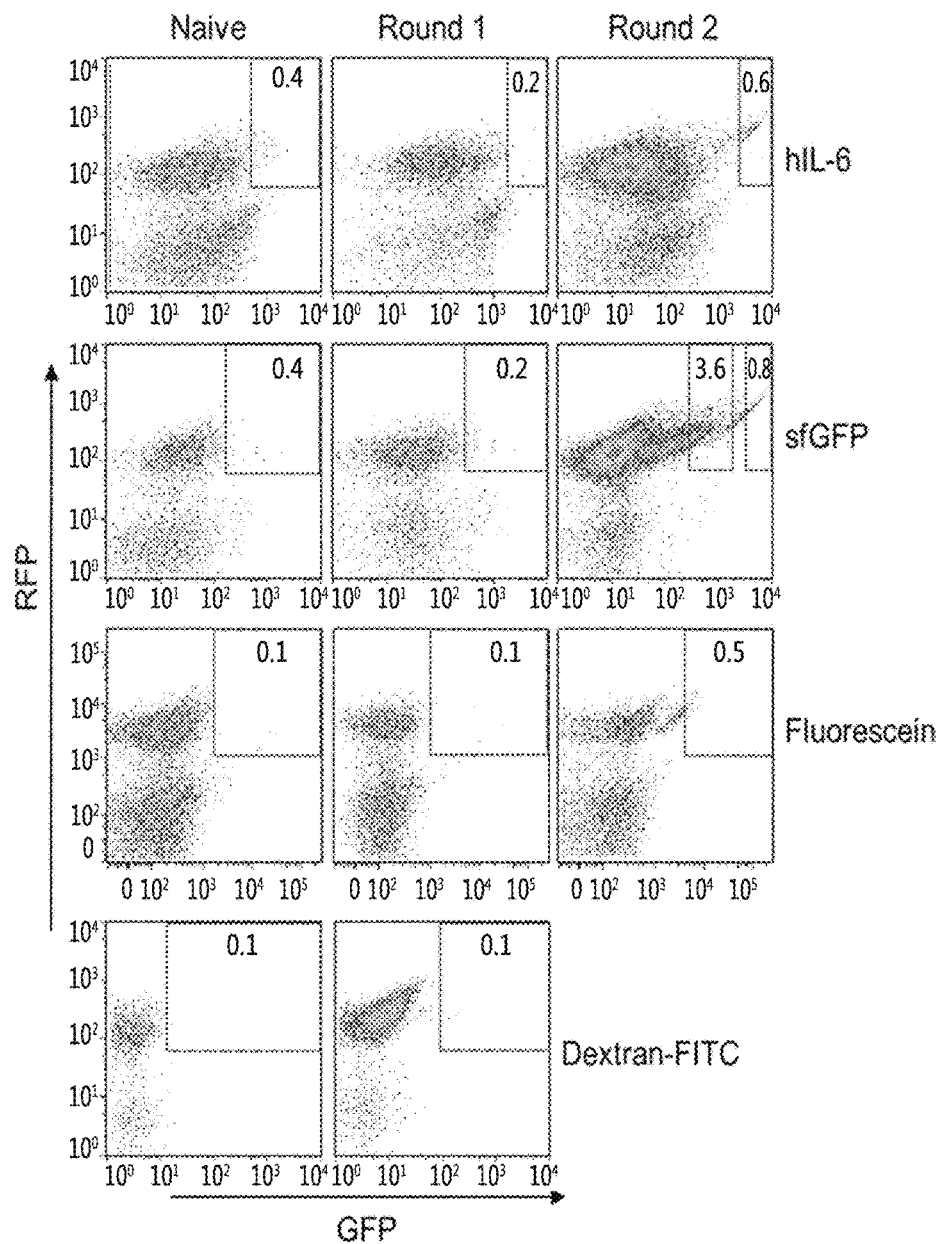

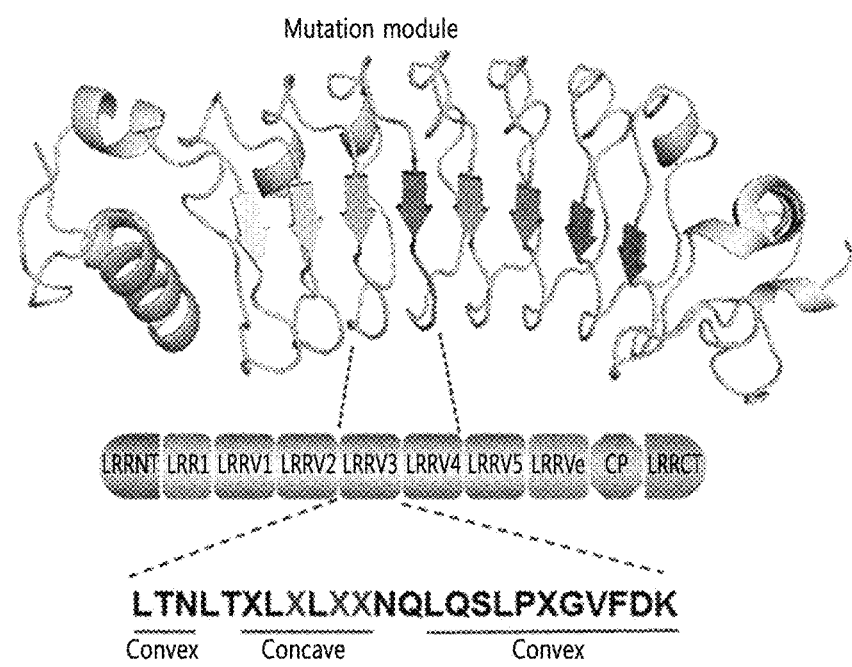
[FIG. 15b]

[FIG. 15c]
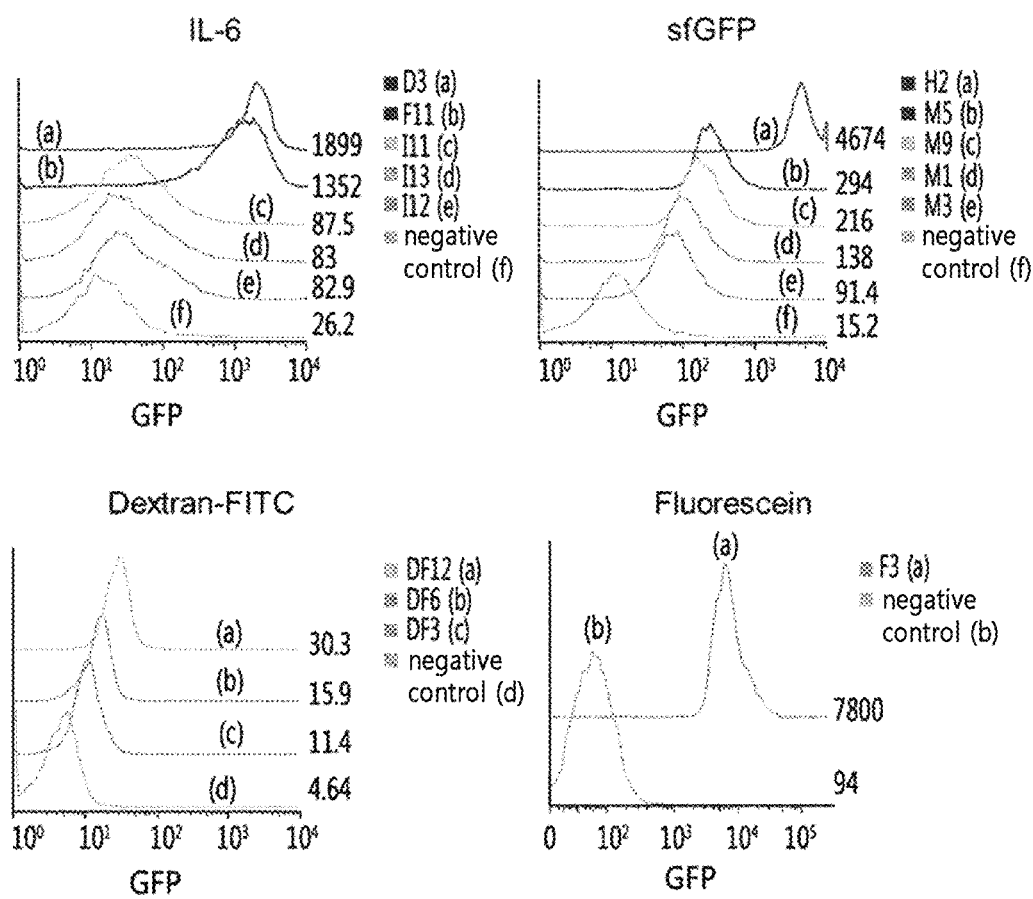

[FIG. 16]
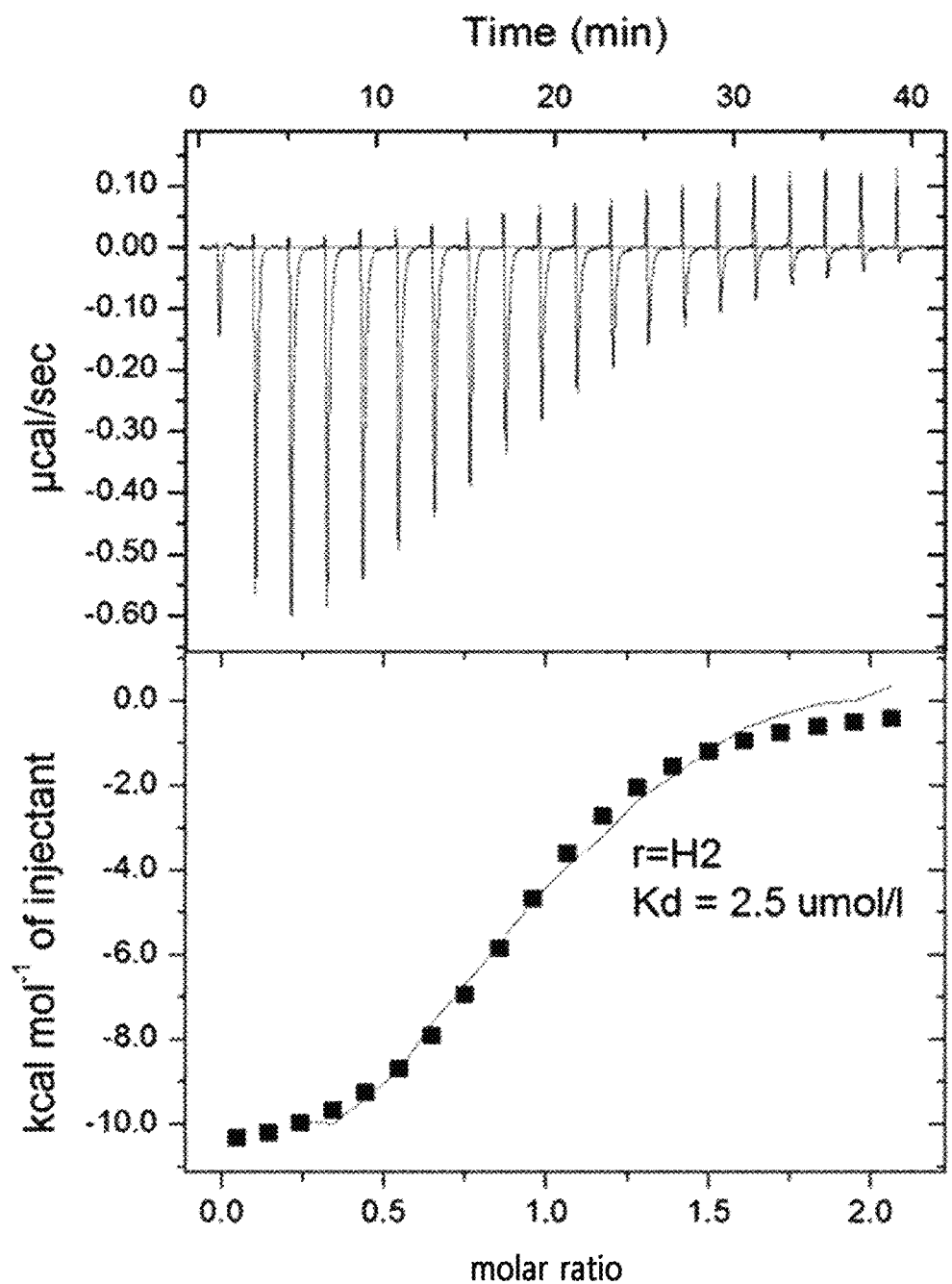

[FIG. 17]
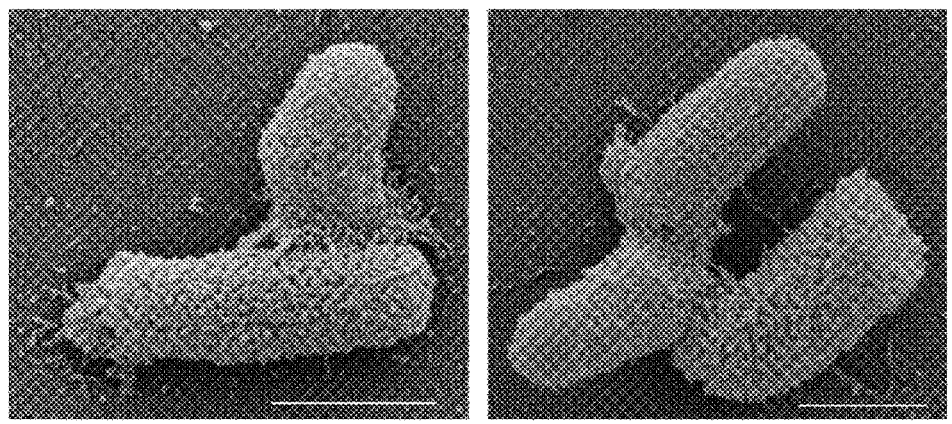

[FIG. 18]

| | In vitro | | In vivo | |
|---|---|---|---|---|
| | ribosome display | phage display | yeast display | protein fusion display |
| marker | 1 | 1~5 copies | $10^4$~$10^5$ copies | ≥ $10^5$ copies |
| library general max. size | $10^{12}$ ~ $10^{13}$ | $10^{10}$ ~ $10^{11}$ | $10^7$ | $10^7$ |
| Genotype-phenotype linking | ribosome inclusion bodies | phage particles | cells | active inclusion bodies |
| protein labeling | mRNA | cell surface | cell surface | active inclusion bodies in cytoplasm |
| characteristics | • library size is big<br>• rapid rate (library does not require transformation) | • screening of a library of big-sized proteins<br>• easy to handle | • Quality control using secretion mechanism in eukaryotic cells<br>• minimization of avidity phenomenon<br>• large-scale library screening using FACS | • a large number of binding proteins -> high specificity<br>• protein secretion mechanism not necessary -> the size of proteins being displayed is not limited<br>• high signal-to-noise ratio |
| limitations | • limitation on selection scope<br>• instability of ribosome complex<br>• limitation on protein size | • presence of a possible risk that the binder with high binding affinity may not be eluted<br>• multivalent labeling -> avidity effect<br>• high false-positive rate<br>• require a fixed motif | • low transformation efficiency -> small library size<br>• require protein secretion -> limitation on protein size<br>• differentiated saccharification | |
| assay | Binding to affinity matrix | Binding to affinity matrix | FACS | FACS |

* Nat Biotechnol. 2005 Sep;23(9):1105-16
* Angew Chem Int Ed. 2002, 41, 4402 ± 4425

[FIG. 19]
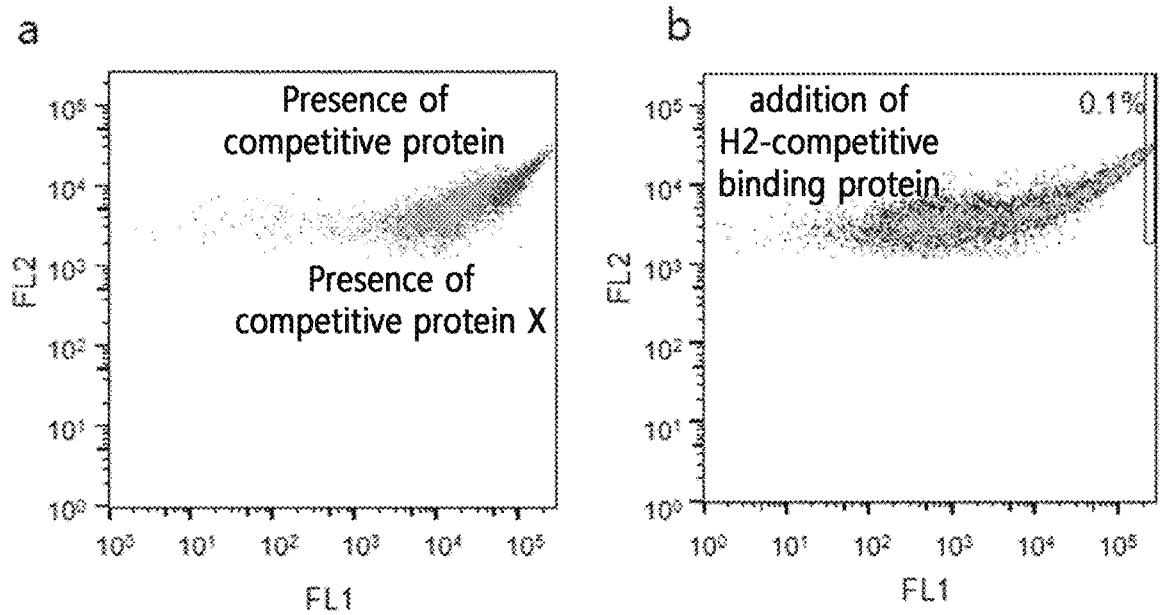
[FIG. 20]
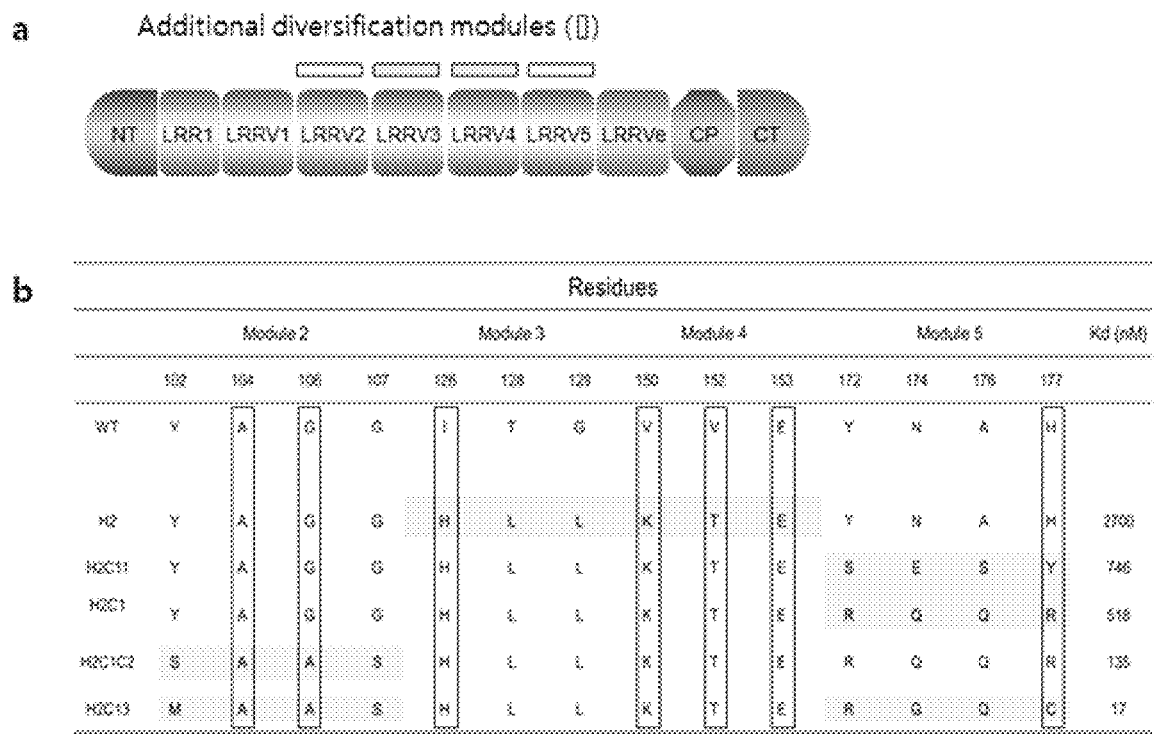

[FIG. 21]
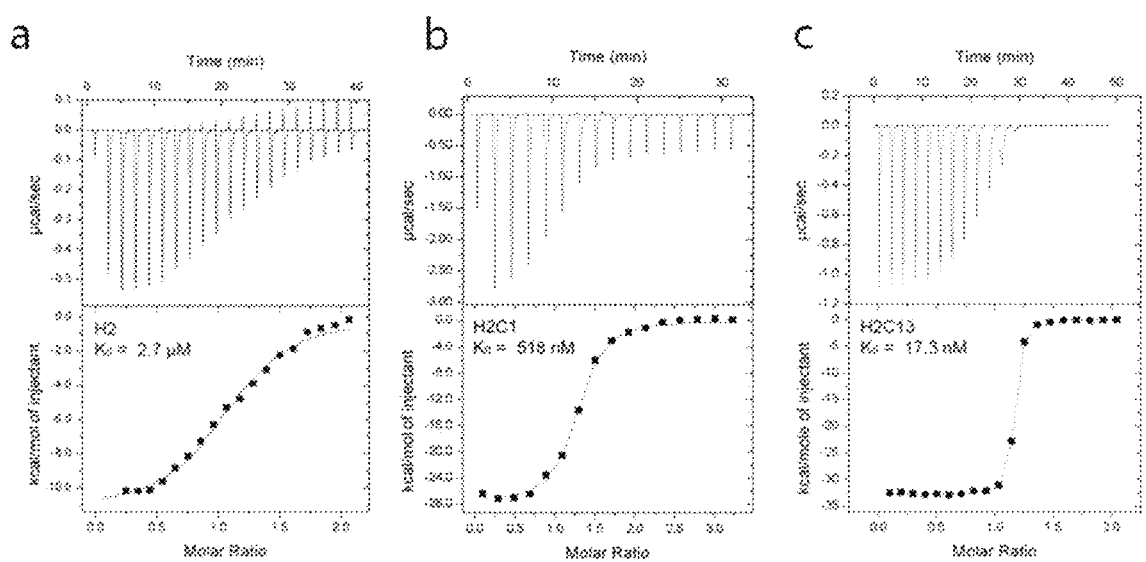

[FIG. 22]
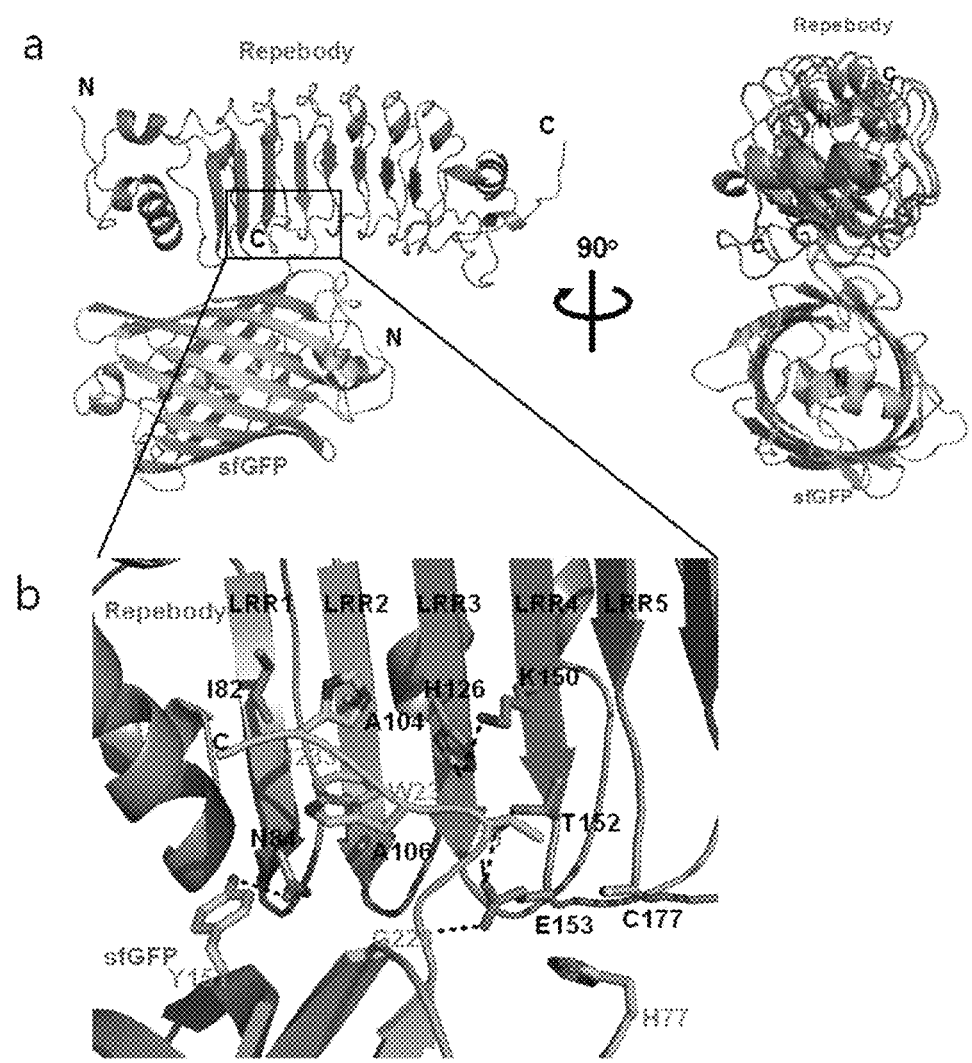

[FIG. 23]
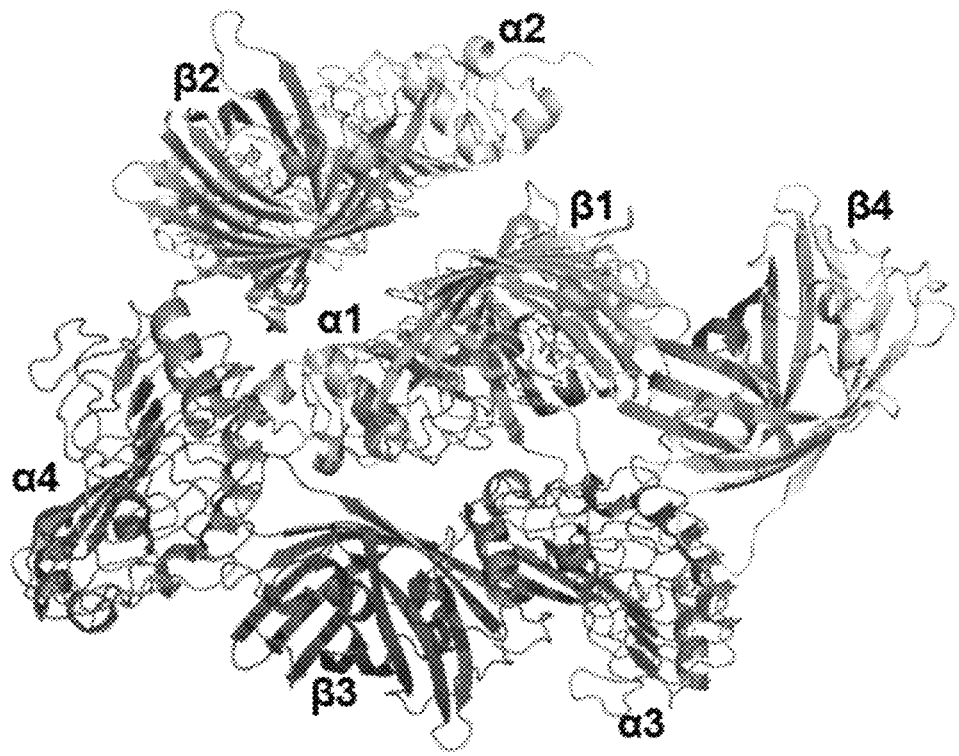
[FIG. 24]
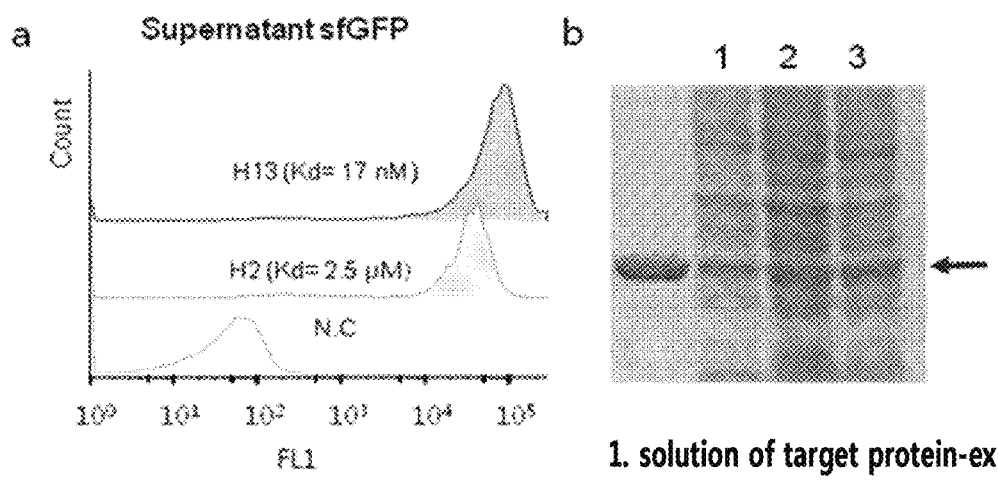
1. solution of target protein-expressing cells
2. whole cells after ultrasonification
3. supernatant of cells after ultrasonification

ANALYSIS METHOD OF MOLECULAR INTERACTIONS ON PROTEIN NANOPARTICLES USING FLOW CYTOMETRY

TECHNICAL FIELD

The present invention relates to a method for analyzing the interaction between a binding protein and a target material, including measuring the interaction between the binding protein and the target material using an interaction trapper (IT) cell. The IT cell has the binding protein displayed on the surface of intracellular inclusion bodies, i.e., insoluble aggregates, by expressing a fusion protein which forms active protein particles containing the binding protein. The method includes increasing cell permeability without affecting the activity of the binding protein displayed on the active inclusion bodies and genetic information. Additionally, the present invention relates to a method for screening a library, further including a step of recovery by an individual cell unit. Furthermore, the present invention is characterized by introducing a target material from the outside of a cell thereinto while conserving genetic information and the activity of the binding protein displayed on the surface of intracellular inclusion bodies. Additionally, the present invention relates to a cell and a cell library in which include a construct containing a polynucleotide encoding the fusion protein or a binding protein displayed on the active inclusion bodies by expressing the fusion protein.

BACKGROUND ART

All processes carried out by living organisms are established by interaction network complexes mediated by intracellular proteins (interactomes). Any problem in the control of the interaction can influence the entire network and may cause a disease. Accordingly, it is a platform to understand and control the proteins involved in the interaction for the understanding of the network complexes, and it is also very important for the studies of disease treatment and the development of therapeutic agents.

In this regard, various screening methods for understanding in-vivo protein interactions have been studied by constructing protein libraries (interaction partners of intracellular proteins) by targeting the intracellular proteins with known functions and characteristics, selecting only the proteins which interact with the targets from the libraries, and confirming their characteristics (Hening Lin and Virginia W. Cornish., 2002. Screening and Selection Methods for Large-Scale Analysis of Protein Function. *Angew. Chem.* Int. Ed 41; 4402-25).

Currently, most library screening methods can be largely divided into a cell-free system and a surface display system. As conventional library screening methods, examples of the representative cell-free system may include ribosome display and in-vitro compartmentalization (IVC) methods and examples of the surface display system may include phage display and bacteria/yeast display methods.

First, ribosome display is a method for forming an mRNA-ribosome-peptide triple complex, dissociating peptides bound to a target from the complex, and amplifying the mRNA of the peptides by RT-PCR. Ribosome display has an advantage in that it can provide a library with a maximum size up to $10^{13}$ because the entire process is carried out in-vitro, and thus does not require transformation. However, there are disadvantages in that only 27% is present as complexes, and the protein size to be displayed on the mRNA-ribosome is limited, and there are limits in terms of stability of ribosome complexes and technical sensitivity, etc. (Hanes, J and Pluckthun, A., 1997. In vitro selection and evolution of functional proteins by using ribosome display. *Proc. Natl. Acad. Sci.* 94: 4937-42).

In-vitro compartmentalization (IVC) is a method for compartmentalizing genes based on the aqueous emulsion dispersed in oils instead of in-vivo, and the compartmentalized genes are transcribed and translated within the emulsion, thereby forming a protein library. At least $10^9$ droplets can be made with a volume of 1 mL, and can have the role of an independent microreactor which is stable at various external conditions (temperature, pH, and salt concentration). However, the emulsion can be destroyed using an organic solvent during protein recovery, and the organic solvent used may reduce the activities of proteins, and the thus-recovered proteins may not exhibit activities in-vivo (Dan S. Tawfik and Andrew D. Griffiths, 1998. Man-made cell-like compartments for molecular evolution. *Nat. Biotechnol.* 16; 652-56).

Phage display, which is most conventionally used in library screening at present, is a method for screening libraries based on the binding affinity of the library proteins to an immobilized target using the library proteins displayed on the pIII protein at the end of the phage. Phage display has an advantage in that it can easily screen a large number of clones in libraries. However, since 1 to 5 binding proteins are displayed on the pIII protein of phage and a target is used after immobilizing it to beads and plate bottom, several bindings may occur simultaneously, thereby causing an avidity effect, i.e., a problem showing a difference in the real affinity of an individual protein to the target. Additionally, due to the characteristics of the method, an elution step is required. In this regard, there is a limit in that the displayed protein cannot be easily eluted from the immobilized phase when the displayed protein has a high binding affinity to the target. Additionally, the panning method used for screening libraries in phage display has a limit in that it has a low signal-to-noise ratio, and thus at least 3 to 5 panning processes are required for obtaining proteins having binding affinity to the target. Further, there is a limit in that it has a high false positive rate (George P. Smith and Valery A. Petrenko, 1997. Phage Display. *Chem. Rev.* 97: 391-410).

Surface display, which was developed to overcome the limits of phage display, is a method for stably expressing proteins on the surface of a microorganism using a surface protein of a microorganism such as bacteria and yeasts, as a surface anchoring motif. The surface display method has an advantage in that it enables high-throughput screening ($1 \times 10^9$ cells/h) due to the use of fluorescence-activated cell sorting (FACS) when screening libraries using a fluorescence probe-conjugated target, and also has a lower non-specific background compared to the panning method of phage display.

However, the surface display system requires that the protein library be successfully projected outside of the cell wall, and simultaneously, that the proteins which have successfully passed through the membrane be stably displayed on the cell surface and have no three-dimensional structural change in the proteins displayed to the cell surface (i.e., maintain protein activities). For this purpose, a very effective signal sequence that can help the proteins pass through the membrane for their arrival at the cell surface must be fused to the proteins. Further, the proteins need to be successfully projected outside of the cell, and thus the surface display system has limits with respect to the protein size and the number of proteins to be displayed on the cell surface, etc., (Eric T. Boder and K. Dane Wittrup, 1997. Yeast surface display for screening combinatorial polypeptide libraries. *Nat. Biotech.* 15; 553-57).

Accordingly, to overcome the limits of the existing screening systems, it is necessary to develop an effective and efficient screening system which has improved screening sensitivity, enabling screening of targets having various binding affinities (in the range of a few millimoles to a few nanomoles), and which has a high signal-to-noise ratio to enable easy screening of the desired proteins and binding proteins having specific bindings among the numerous intracellular proteins from libraries.

To resolve the problems described above, a method was suggested wherein the detection signal is amplified when linking several binding proteins to a target by immobilizing them to a single matrix, and wherein the signal-to-noise ratio is increased using a fluorescence-mediated detection method. Examples of the analysis methods developed with these characteristics may include a method of interactive detection between materials by nanoassembly using ferritin, a protein having a self-assembly property (Sangkyu Lee et al., 2011. Small-Molecule-Based Nanoassemblies as Inducible Nanoprobes for Monitoring Dynamic Molecular Interactions Inside Live Cells. *Angew Chem Int Ed Engl* 50; 8709-13), a method of using nanoparticles as an immobilized matrix for their utilization in interactions and catalytic actions with biological molecules (Wenwan Zhong, 2009. Nanomaterials in fluorescence-based biosensing, 394; 47-59).

Recently, studies were reported utilizing biocatalysis by immobilizing the enzymes into inclusion bodies (IBs), which are insoluble precipitates of intracelluarproteins (Jozef Nahalka, Bernd Nidetzky, 2007. Fusion to a pull-down domain: a novel approach of producing trigonopsis variabilis D-amino acid oxidase as insoluble enzyme aggregates. *Biotechnology and Bioengineering.* 97; 454-61).

Inclusion bodies (IBs) generally refer to inactive aggregates; however, according to a recent report, some inclusion bodies are active protein particles capable of maintaining most of the intrinsic biochemical properties of proteins (Antonio Villaverd et al., 2005. Aggregation as bacterial inclusion bodies does not imply inactivation of enzymes and fluorescent proteins. *Microbial Cell Factories* 4; 1-6). 0 Enzymes and fluorescent proteins were immobilized using the active protein particles as an immobilized matrix and then the activities of enzymes and fluorescent proteins were measured. The result showed that their activities were maintained at 30% to 100%, compared to the activities of the non-immobilized enzyme and the fluorescent protein, thus confirming effectiveness of improved stability and the recyclability, etc. on immobilized enzymes. Accordingly, studies are underway in the utilization of the active protein particles in the enzyme industry.

Previously, the present inventors confirmed that family II cellulose-binding domain (CBD) derived from *Cellulomonas fimi* forms inclusion bodies (IBs) via self-aggregation in *Escherichia coli* (*E. coli*). As a result, they developed a method for observing the interactions between biomolecules in-vivo using the phenomenon that the proteins simultaneously expressed in eukaryotic cells as well as in bacterial cells are simultaneously accumulated in the inclusion body particles (Korean Patent Application Publication No. 10-2013-0023057). However, the above method has limits in that it only allows observation of the interactions between intracellular biomolecules expressed simultaneously in-vivo. Furthermore, due to its low signal-to-noise ratio, it is difficult to effectively compartmentalize and recover the binding material as an individual cell unit after it has interacted with the target material. Additionally, the method has a limit in that the target material must be limited to materials that can be synthesized in cells, such as proteins, peptides, nucleic acids, etc., and that only fluorescent proteins must be used as the fluorescence signal. That is, the method has disadvantages in that various forms of target materials introduced from the outside cannot be used, and that various kinds of fluorescent chemical materials cannot be used.

DISCLOSURE

Technical Problem

The present inventors have developed a system which enables a direct observation of the interactions occurring between biomolecules and foreign materials by increasing the permeability of a cell wall to prevent any influence on the activity of the binding proteins displayed on the inclusion bodies and genetic information, and introducing a foreign target material into a cell to interact with the binding proteins displayed on the inclusion bodies present in the cell. As a result, they have confirmed that the signal-to-noise ratio was improved 450-fold or more, thus enabling a direct observation of the interactions between materials at the single-cell level. Additionally, the present inventors have in fact constructed a library and performed screening. As a result, they have confirmed that binding proteins capable of interacting with a target protein can be selectively recovered via high-throughput screening of the interactions between molecules, and that high-affinity binders can be detected at a nanomolar level by repeating the screening two times at maximum, thereby completing the present invention.

Technical Solution

An object of the present invention provides a method for analyzing the interaction between a binding protein and a target material, including:
  (a) providing a cell which includes a construct containing a polynucleotide encoding a fusion protein consisting of the binding protein and an active inclusion body protein;
  (b) expressing the fusion protein in the cell, thereby forming an interaction trapper (IT) cell, wherein the binding protein is displayed on the inclusion body;
  (c) introducing a fluorescence material-conjugated target material into the cell according to step (b); and
  (d) measuring the interaction between the binding protein and the target material which is introduced from the outside of the cell, based on the fluorescence intensity of the fluorescence material conjugated to the target material.

Another object of the present invention provides a method for screening a cell specific to a target material, including analyzing the interaction between the binding protein and the target material by the above analysis method and recovering the cell by an individual cell unit.

Still another object of the present invention provides a method for screening and/or preparing a binding protein specific to a target material, including isolating a gene encoding a binding protein specific to a target material in the cell recovered by the above screening method.

Still another object of the present invention provides a cell which includes a construct containing a polynucleotide encoding a fusion protein consisting of a binding protein and an active inclusion body protein.

Still another object of the present invention provides a cell library, which includes a construct containing a polynucleotide encoding a fusion protein consisting of a binding protein and an active inclusion body protein.

Still another object of the present invention provides an interaction trapper (IT) cell and a cell library, wherein a fusion protein consisting of a binding protein and an active inclusion body protein is expressed and the binding protein is displayed on the inclusion body.

Advantageous Effects

The method of the present invention enables a sensitive labeling of a target material, which interacts due to the overexpression of a binding protein, and thereby provides an improved screening efficiency due to a significantly higher signal-to-noise ratio (a 450-fold increase) compared to the conventional screening methods. The method of the present invention also enables easy isolation of cells by an individual cell unit, and thus can provide a high-throughput screening (HTS) technology to screen and isolate interacting proteins from a large number of libraries using a fluorescence microscope and a flow cytometer. Additionally, the interactions between biomolecules in any foreign target material with difficulty of in-vivo expression can be readily analyzed at high speed by introduction thereof into cells after extracellular expression. The present invention can be used in various fields, including the development of antibodies/artificial antibodies, preparation of novel interacting proteins, and analysis and optimization of the interactions between target proteins and drug candidates.

BRIEF DESCRIPTIONS OF THE DRAWINGS

FIG. 1 shows the representative drawing of the present invention illustrated in a schematic diagram, which shows the intracellular particle display enabling high-speed analysis between materials and the results of analysis of interactions between materials using the same.

In FIG. 2, A shows an entire schematic diagram of intracellular particle display technique from the methodological point of view. Additionally, in B of FIG. 2, the 'a' shows a schematic diagram, in which a binding protein (repebody) and a red fluorescent protein (mRFP) are fused and displayed in active inclusion bodies; the 'b' shows an electron microscope image of cells, in which the protein inclusion bodies (CBD-IBs) of the 'a' are expressed; and the 'c' shows a fluorescence microscope image of cells, in which the protein inclusion bodies of the 'a' were expressed (blue: genomic DNA). Additionally, the 'd' shows a schematic diagram of the protein inclusion bodies isolated from the cells of the 'b' by ultrasonication; and the 'e' shows a schematic diagram illustrating the generation of cracks in the cells when they underwent the process of increasing cell permeability according to the method of the present invention.

FIG. 3 shows fluorescence microscope images of the interaction trapper (IT) cells, in which a binding protein (VLR) and a fluorescent protein (mRFP) are displayed using a CBD protein capable of forming active inclusion bodies, and only the inclusion bodies isolated from the IT cells by ultrasonication FIG. 4 shows the results of flow cytometry analysis, confirming the effect of a cell-thawing/freezing process developed in the present invention on increasing cell permeability according to the presence/absence of active inclusion body display of the binding protein.

FIG. 5 shows the results of flow cytometry analysis, confirming that the cell freezing process during the process developed in the present invention for increasing cell permeability, could maintain the activity and expression of the binding protein displayed on the active inclusion bodies, but it was not sufficient to introduce a foreign target material.

FIG. 6 shows the results of flow cytometry analysis confirming the introduction of a foreign target material by treating the inclusion body cells, which underwent a cell-freezing process, with an acidic solution during the process of increasing cell permeability developed in the present invention, in which A and B show the results of the introduction of a foreign target material according to the kind and pH of the acidic solution, and C shows the result of a permeability analysis between EDTA (a chelating agent capable of penetrating external cell membranes) and acidic solutions.

FIG. 7 shows the results confirming the interactions between a binding protein and a foreign target material introduced into a cell by the optimized permeability in FIG. 6, in which A shows the fluorescent images confirming the interactions between the binding protein and the target material, and B shows the result confirming the level of intracellular introduction of the target material according to the culture hours after increasing the permeability of the IT cells through the interactions between the target material and the binding protein based on the fluorescence intensity of the target material.

FIG. 8 shows the results of flow cytometry analysis confirming that the interaction between the binding protein and the target material is a specific binding capable of maintaining the intrinsic property by the active inclusion bodies through the optimized method of increasing cell permeability.

FIG. 9 shows the results of observation of the intracellular and extracellular changes by increasing cell permeability of the active inclusion body cells, in which A in FIG. 9 shows the results of the changes in the intracellular proteins by increasing cell permeability analyzed using the protein analysis system, Experion™ Pro260 (Bio-rad), and B in FIG. 9 shows the results of the changes in the active inclusion body cells before and after increasing cell permeability observed under an electron microscope.

FIG. 10 shows the results confirming that the genetic information of intracellular binding proteins was mostly maintained due to the active inclusion bodies even after the process of increasing cell permeability developed in the present invention, based on quantitative PCR (RT-PCR).

FIG. 11a shows the results confirming the intracellular particle display which underwent the process of increasing cell permeability developed in the present invention using a model protein and a model target material, and shows the results of flow cytometry analysis and fluorescence images confirming the interactions between the binding protein and the target material due to the introduction of a foreign target material by increasing cell permeability.

FIG. 11b shows the results confirming the intracellular particle display which underwent the process developed in the present invention for increasing cell permeability using a model protein and a model target material, and shows the results confirming that most of the genetic information of binding proteins in the IT cells was maintained even after the process of increasing cell permeability developed in the present invention, analyzed based on quantitative PCR (RT-PCR) and agarose gel electrophoresis.

FIG. 11c shows the results confirming the intracellular particle display which underwent the process of increasing cell permeability developed in the present invention using a model protein and a model target material, and shows the results confirming the changes in the active inclusion body cells before and after increasing cell permeability observed using a flow cytometer and an electron microscope.

FIG. 12 shows the analysis results for confirming the size of the cell permeable foreign target by the process of increasing cell permeability developed in the present invention via dextran-FITC treatment having various kinds of molecular weight using C20, which is a dextran-FITC binder obtained by the intracellular particle display technique.

FIG. 13 shows the fluorescence images (A) and the results (B) of a flow cytometer analysis for interactions between proteins according to the presence/absence of affinity for a binding protein by introducing a target material into a cell using the optimized method developed in the present invention for increasing cell permeability. Additionally, C in FIG. 13 shows the results that the fluorescence intensity of the fluorescence material conjugated to the target material increased along with the increase in the affinity of the binding protein. Additionally, D and E in FIG. 13 show the results confirming the interaction between proteins using SDS-PAGE, in which the band of the target material was confirmed only when there was an interaction between the target material and the binding protein (lane 1: cells expressing InVLR5c-mRFP-cex; lane 2: cells expressing mGFP-IL6; lane 3: permeabilized InVLR5c-mRFP-cex cells, which had no affinity for IL-6, with treatment of mGFP-IL6 proteins for interacting; and lane 4: permeabilized D3E8-mRFP-cex cells, which had affinity for IL-6, with treatment of mGFP-IL6 proteins for interaction).

FIG. 14 shows the results confirming that libraries can be screened using intracellular particle display. Illustrated are the results of screening efficiency analyzed by PCR amplification using recovered 10,000 E. coli cells (PPI+) with high GFP fluorescence by a flow cytometer. Specifically, a library-analogous environment was made by mixing inclusion body cells (PPI+) with an interaction between a binding protein and the target material; and inclusion body cells (PPI−) without an interaction between a binding protein and the target material. And then the cells which expressed a binding protein having an interaction with a target material, were analyzed by the fluorescence of GFP conjugated to the target material.

FIG. 15a shows the results of screening performed using real libraries via intracellular particle display, and illustrated are the results of the screening process looking for protein binders for various kinds of targets.

FIG. 15b shows the results of screening performed using real libraries via intracellular particle display, and illustrated is a schematic diagram of the entire structure, in which amino acid residues are indicated, for the construction of a random library of repebody used as a model binding protein.

FIG. 15c shows the results of screening performed using real libraries via intracellular particle display, and confirmed the interactions between each of the selected protein binders from the library screening and targets using a flow cytometer.

FIG. 16 shows the measurement results of binding affinity of H2, which is an sfGFP protein binder obtained as a result of screening the real libraries, by isothermal titration calorimetry (ITC).

FIG. 17 shows the images of active inclusion bodies proteins of a CBD observed under an electron microscope, in which the formation of the gigantic CBD active inclusion bodies by the aggregation of a large number of nanoparticles with a size of 20 nm to 30 nm was observed (scale bar: 1 μm).

FIG. 18 shows the comparison results between the library screening system of the present invention and the conventional library screening systems.

The 'a' in FIG. 19 shows the result confirming that the fluorescence value was reduced when a competitive binding protein was treated in the intracellular particle display technology, and the 'b' in FIG. 19 shows the result of screening of binding proteins with matured affinity by an affinity-competitive screening using H2 repebody as a competitor.

FIG. 20 relates to a library construction of binding proteins for affinity maturation, in which the 'a' shows a schematic diagram of modules where a mutation occurs in the repebody (an LRR protein), which is an sfGFP (LRRV3 and LRRV4: a H2 repebody mutation module; LRRV2 and LRRV5: a mutation module in H2 repebody for affinity maturation), and the 'b' shows a table illustrating the amino acid sequences and binding affinities of binding proteins with mutations with reference to InVLR5c (WT).

FIG. 21 shows the results of binding affinities of sfGFP binders with increased affinity by competitive screening, measured by isothermal titration calorimetry (ITC).

FIG. 22 shows the crystal structure of the binding protein with a target protein (sfGFP) complex.

FIG. 23 shows the pattern of crystal packing in the target protein (sfGFP) and binding protein (H2C13) complex in the asymmetric unit (α: H2C13 binding protein; β: sfGFP target protein).

FIG. 24 shows the result (a) of flow cytometry analysis for the interaction between protein binders and target proteins using the supernatants (b in FIG. 24) of cells after ultrasonication and the result (b) of SDS-PAGE analysis of an unpurified solution containing a target protein (sfGFP).

BEST MODE

To achieve the above objects, in an aspect, the present invention provides a method for analyzing the interaction between a binding protein and a target material, including:

(a) providing a cell, which comprises a construct comprising a polynucleotide encoding a fusion protein consisting of the binding protein and an active inclusion body protein;

(b) expressing the fusion protein in the cell, thereby forming an interaction trapper (IT) cell, wherein the binding protein is displayed on the inclusion body;

(c) introducing a fluorescence material-conjugated target material into the cell according to step (b); and (d) measuring the interaction between the binding protein and the target material which is introduced from the outside of the cell, based on the fluorescence intensity of the fluorescence material conjugated to the target material.

In an exemplary embodiment, the present invention provides a method further including increasing permeability of the cell according to step (b) before step (c).

In another exemplary embodiment, the present invention provides a method wherein the increasing includes making the cell membrane or the cell wall cracked.

In still another exemplary embodiment, the present invention provides a method, wherein the making the cell membrane or the cell wall cracked includes:

(i) freezing the cell according to step (b);
(ii) thawing the frozen cell; and (iii) treating the thawed cell with an acidic solution or chelating agent.

In still another exemplary embodiment, the present invention provides a method wherein the increasing allows the target material to be introduced into the cells without affecting the activity of the binding protein displayed on the intracellular inclusion body and genetic information of the binding protein.

In still another exemplary embodiment, the present invention provides a method wherein the target material is a protein, a nucleic acid, or a compound.

In still another exemplary embodiment, the present invention provides a method wherein the fusion protein further contains a fluorescent protein.

In still another exemplary embodiment, the present invention provides a method wherein the fluorescent protein and the fluorescence material conjugated to the target material have mutually different wavelengths.

In still another exemplary embodiment, the present invention provides a method wherein the active inclusion body protein is a cellulose-binding domain (CBD) protein.

In still another exemplary embodiment of the present invention, the fluorescent protein is selected from the group consisting of green fluorescent protein (GFP), enhanced green fluorescent protein (EGFP), modified green fluorescent protein (mGFP), red fluorescent protein (RFP), monomeric red fluorescent protein (mRFP), enhanced red fluorescent protein (ERFP), *discosoma* sp. red (DsRed) fluorescent protein, blue fluorescent protein (BFP), enhanced blue fluorescent protein (EBFP), cyan fluorescent protein (CFP), cyan green fluorescent protein (CGFP), enhanced cyan fluorescent protein (ECFP), yellow fluorescent protein (YFP), enhanced yellow fluorescent protein (EYFP), azami green (AzG), *Heteractis crispa* red fluorescent protein (HcRed), and blue fluorescent protein (BFP).

In still another exemplary embodiment of the present invention, the fluorescence intensity of the cell is measured using a fluorescence microscope or flow cytometer.

In still another exemplary embodiment of the present invention, step (c) is performed by treating the cell according to step (b) with a solution containing a target material.

In still another exemplary embodiment of the present invention, step (c) further includes introducing a competitive binding protein into a cell.

In still another exemplary embodiment, the present invention provides a method, including analyzing the interaction between the binding protein and the target material by the above analyzing method and recovering the cell by an individual cell unit.

In still another exemplary embodiment, the present invention provides a method wherein the cell is a cell library.

In still another exemplary embodiment, the present invention provides a method for screening and/or preparing a binding protein specific to a target material, including isolating a gene encoding a binding protein specific to a target material in the cell recovered by the above screening method.

In still another exemplary embodiment, the present invention provides a method wherein the isolating a gene further includes amplifying the isolated gene.

In another aspect, the present invention provides a method for method for screening a library specific to a target material, including:

(a) providing a cell library including a construct, which contains a polynucleotide encoding a fusion protein consisting of a binding protein and an active inclusion body protein;

(b) expressing the fusion protein in the cell library, thereby forming interaction trapper (IT) cells, wherein the binding protein is displayed on the inclusion body;

(c) introducing a fluorescence material-conjugated target material into the cells according to step (b) by increasing cell permeability; and (d) measuring the interaction between the binding protein and the target material based on the fluorescence intensity of the fluorescence material conjugated to the target material and recovering the cell by an individual cell unit.

The method of screening libraries of the present invention may further include obtaining fusion proteins present in the cells recovered in an individual cell unit, and isolating and amplifying genes encoding the fusion proteins. The protein recovery or isolation and amplification of genes may be performed by any method widely used in the art.

The above method of the present invention can replace the conventional library screening methods such as ribosome display, phage display, and cell surface display. The method of the present invention is a method for analyzing interactions capable of easily detecting interactions by direct observation of the phenomenon that a foreign target material is co-localized in the active inclusion bodies with the binding protein displayed on the inclusion bodies, in which active protein particles containing the binding protein, i.e., a CBD protein tag, are formed into inclusion bodies within a cell to be used as IT cells. In particular, the method of the present invention has advantages in that it allows overexpression of the intracellular binding proteins into inclusion bodies with high density ($\approx 10^6$ proteins/cell, cf) and sensitive labeling of the target material interacting with the binding protein than the yeast surface expression system ($3 \times 10^4$ proteins/cell), thus providing a higher screening efficiency due to a significantly high signal-to-noise ratio compared to the conventional screening methods, and also being applicable to various binding affinities. Additionally, the method of the present invention has advantages in that it provides high signal intensity even with a trace amount of a target material and thus can confirm the interaction with a target material having a low expression rate; and it is a high-throughput screening system, which can analyze the cells having interactions between the target material and the binding protein based on the fluorescence conjugated to the target material using a flow cytometer and can screen libraries with easy experiments and simple methods because it is an *E. coli*-based system.

The present inventors confirmed that the family II cellulose-binding domain (CBD) derived from *Cellulomonas fimi* is self-aggregated to form inclusion bodies within *E. coli*. They had previously developed a method for observing interactions between intracellular biomolecules using the phenomenon that the proteins simultaneously expressed in eukaryotic cells as well as in bacterial cells are simultaneously accumulated into the inclusion body particles (Korean Patent Application Publication No. 10-2013-0023057).

Accordingly, the present inventors in the above patent application formed IT cells, in which binding proteins with intrinsic properties (antibodies, antibody mimics, interacting proteins, ligand-binding proteins, drug-target proteins, etc.) were displayed, using a CBD protein capable of trapping interactions by the active inclusion bodies. The present inventors have developed a protein library screening system, which enables a direct observation of the interactions between the fluorescence-conjugated target materials (e.g., proteins, nucleic acids, compounds, or low molecular weight materials) and the binding proteins displayed on the inclusion bodies by introducing the target materials from the outside into the cells by the optimized method of increasing cell permeability developed in the present invention, and also enables a selective recovery of the binding proteins interacting with the target materials via high-throughput detection of molecular interactions at the single-cell level (FIG. 1).

In particular, the process of increasing cell permeability developed as a special feature in the present invention is characterized by being capable of stably maintaining genetic information of the binding proteins within the cells without losing most thereof while stably maintaining the activities and expression of the binding proteins displayed on the active inclusion bodies within the cells.

Generally, the process of increasing cell permeability is a method for increasing the permeability of a cell wall/membrane by a chemical/physical method or a method for extracellular secretion of in-vivo biomolecules by perfectly removing the cell wall/membrane. That is, it may be a method for perfectly disrupting a cell by osmosis, an ultrasonic crusher, etc., or a method for extracellular secretion of the genetic information as well as the intracellular proteins while maintaining the cell shape using toluene, etc. (Hansruedi Felix, 1982. Permeabilized cells. *Analytical Biochemistry* 120; 211-34).

The optimized method of increasing cell permeability developed in the present invention is characterized in that even after increasing cell permeability to the degree that free movement is allowed, the intracellular/extracellular proteins do not lose the binding proteins displayed on the active inclusion bodies and the genetic information to the outside of the cell and maintain the cell shape.

Additionally, in an exemplary embodiment of the present invention, it was confirmed that the presence of active inclusion bodies can affect the presence of genetic information in the binding proteins, and this result agrees with a previous report that ribosomal RNA, RNA polymerase, etc., are discovered in the inclusion bodies (Ursula Rinas and James E. Bailey, 1992. Protein compositional analysis of inclusion bodies produced in recombinant *Escherichia coli*, *Applied Microbiology and Biotechnology* 37; 609-14).

That is, the present inventors have overcome the limitations of the existing surface expression systems (the size and number of proteins for display and the problem of cell surface secretion) by overexpressing the binding protein within a cell. The binding protein, which is displayed in inclusion bodies in high density, has an advantage in that it can sensitively label the target material interacting with the binding protein. Thus, it can show a signal intensity a few hundred to a few hundred thousand times higher than that obtained by the existing cell surface expression, and as a result, has a significantly higher signal-to-noise ratio than the existing screening methods, thereby enabling an easy analysis of interactions between biomaterials (FIG. 18).

Additionally, due to the presence of the binding proteins displayed on the active inclusion bodies, the method of the present invention maintains the endogenous activity of the binding proteins, but also, the genetic information of the binding proteins is rarely lost even after the optimized process of increasing cell permeability developed in the present invention.

As used herein, the term "fusion protein" refers to a protein produced by a fusion between two or more proteins, and in particular, the fusion protein includes binding proteins and CBD proteins. Additionally, the fusion protein of the present invention may be produced by genetic recombination, and specifically, the expression of a binding protein can be confirmed by a method of transforming a construct to a host cell. Additionally, the fusion protein may further include a fluorescent protein.

The construct of the present invention is a recombinant vector to which a polynucleotide encoding the constituting elements of the fusion protein of the present invention is operably connected. As used herein, the term "operably connected" means that the expression control sequence is connected to be able to control the transcription and translation of the polynucleotide encoding the constituting elements of the fusion protein, and it also includes the maintenance of an accurate translation frame so that the constituting elements of the fusion protein encoded by the polynucleotide sequence can be produced by the expression of the polynucleotide under the control of the expression control sequence (including a promoter).

As used herein, the term "binding protein" refers to a protein which can interact with a target material. The binding protein may include a protein that may need to be produced on a large scale for commercial use, and may refer to a binding protein selected from antibodies, antibody mimics, interaction proteins, ligand-binding proteins, drug-targeting proteins, etc., that may become a subject of interaction with a target material, but is not limited thereto. Additionally, the binding protein may refer to not only a native protein that can interact with a target protein, but also a domain or a part of a polypeptide responsible for the binding function, but is not limited thereto.

Specifically, the polynucleotide encoding the binding protein may be one derived from a library including genes encoding various proteins. It may be obtained from the entire genome of a bioorganism, such as an entire genomic DNA and cDNA library. Additionally, the polynucleotides which encode the binding protein and the target material may be obtained from a subset of the entire genome such as a subtracted library or a sized library. For example, the binding protein may be repebody (InB-VLR) family, which is an artificial antibody protein in which the N-terminus of internaline B (InB) protein, a modified repeated module of variable lymphocyte receptor (VLR) protein, and the C-terminus of VLR protein are conjugated together, specifically, In-VLR5-c, In-VLR5c-D3E8, or variants thereof (Korean Patent No. 10-1255682).

As used herein, the term "active inclusion bodies" refers to a protein which has the characteristics enabling the display of a binding protein while maintaining the endogenous activity of the binding protein expressed in the inclusion bodies, for example, cellulose-binding domain (CBD) protein, PhaC protein (polyhydroxybutyrate synthase from *Cupriavidus necator*; Bjorn Steinmann, Andreas Christmann, Tim Heiseler, Janine Fritz, Harald Kolmar, 2010. In Vivo Enzyme Immobilization by Inclusion Body Display. *Appl. Environ. Microbiol.* 76; 5563-69), foot-and-mouth disease virus (FMDV) VP1 capsid protein (Antonio Villaverd et al., 2005. Aggregation as bacterial inclusion bodies does not imply inactivation of enzymes and fluorescent proteins. *Microbial Cell Factories* 4; 1-6), etc., are included.

As used herein, the term "cellulose-binding domain (CBD) protein" refers to a family II protein derived from *Cellulomonas fimi* capable of binding to cellulose. According to an exemplary embodiment of the present invention, the CBD protein may include those proteins which can form inclusion bodies in *E. coli*, form intracellular active particles which do not affect the activities or characteristics of endogenous proteins conjugated thereto, and form all active inclusion bodies without being limited to CBD proteins.

According to an exemplary embodiment of the present invention, D3E8, which is one of the variants of leucine-rich-repeat (LRR) protein InB-VLR (Korean Patent No. 10-1255682), was used as a binding protein. D3E8 is a protein having a binding affinity of 2 nM for IL6 (i.e., a target material), and a protein conjugated to a binding protein was designed as follows. For the production of a fusion protein consisting of only InVLR5c (a binding protein without a binding affinity for IL6), mRFP (a fluorescent protein), and family II CBD, a pInVLR5c-mRFP-CBD plasmid vector was prepared by genetic recombination. For the production of a fusion protein consisting of InVLR5c-D3E8 (a binding protein with a binding affinity for IL6), mRFP (a fluorescent protein), and family II CBD, a pD3E8-mRFP-CBD plasmid vector was prepared by genetic recombination. These vectors were transformed into an E. coli host and used as a factor for producing fusion proteins (Example 2).

As used herein, the term "cell" refers to a basic functional, structural unit of all bioorganisms. The cell may be an animal cell, a plant cell, a yeast cell, or a bacterial cell, and may be a cell of bacteria such as E. coli, Streptomyces, and Salmonella typimurium; a cell of yeasts such as Pichia pastoris; a fungal cell; a cell of insects such as Drosophila and Spodoptera Sf9 cell; a cell of animals such as Chinese hamster ovary (CHO), COS, NSO, 293, bow melanoma cell, although not particularly limited thereto, and specifically, a bacterial cell, and more specifically an E. coli cell. Specifically, the cell of the present invention may be a bacterial cell in which active inclusion bodies are formed by the overexpression of a CBD protein and the active inclusion bodies can be used as IT cells.

As used herein, the term "Interaction Trapper cells (IT cells)" refers to cells which, being transformed with a plasmid capable of expressing a binding protein and a CBD protein, are overexpressed to thereby allow the CBD protein to form inclusion bodies, and the binding protein expressed in the inclusion bodies is displayed in high density while the endogenous activity of the binding protein is maintained. Specifically, the IT cells are those which can interact with the binding protein displayed on the inclusion bodies when the external target material is introduced into the IT cells.

As used herein, the term "a target material" refers to a material which can interact with a binding protein. Additionally, the target material may not only include a native protein which can interact with the binding protein but also a part of a domain or polypeptide responsible for a function or a compound not present in-vivo. In particular, the target material may be a useful candidate material for use in biotechnology, medical sciences, pharmacology, etc., or a material that can cause in-vivo actions, and in particular, a protein, a nucleic acid, or a compound, e.g., IL-6 or sfGFP or fluorescein.

For the purpose of the present invention, the target material is characterized in that it is not expressed simultaneously with a binding protein in a cell but it is introduced from the outside. That is, the inclusion bodies are used as the IT cells capable of displaying the binding protein, and the target material is introduced from the outside.

As used herein, the term "introduction into a cell" refers to the transport of a material from the outside to the inside of a cell by a physical or chemical method. In transporting the external material into a cell, the material is a target material and the transport includes a process of increasing the permeability of a cell membrane or cell wall for the transport of the target material into the cell. There are various physical or chemical methods that can temporarily increase the permeability of a cell membrane or cell wall (HANSRUEDI FELIX, 1982. Permeabilized Cells. *Anal. Biochem.* 120; 211-34), e.g., ultrasonication, osmosis, heat treatment, freezing, thawing, acid solution treatment, chelating agent treatment, or a combination thereof.

In the present invention, the process of increasing permeability may include, without limitation, any method used in the art as long as it enables the introduction of a target material into a cell through a permeabilized membrane without affecting the activity and genetic information of the binding protein displayed on the inclusion bodies within the cell. Additionally, in the present invention, the process of increasing permeability may specifically include making the cell membrane or the cell wall cracked, and more specifically, include:

(i) freezing the cell according to step (b);
(ii) thawing the frozen cell; and
(iii) treating the thawed cell with an acidic solution or chelating agent, but is not limited thereto.

Foreign target materials may be transported into the inside of cells through the cracks generated on the cell membrane or cell wall, but the genetic materials inside the cells can hardly be released out of the cells through the cracks. Therefore, the genes of binding proteins contained in the screened cells can be obtained after screening target material-specific cells.

In the present invention, the freezing may be performed at a temperature of −80° C. to −10° C. or the thawing may be performed at a temperature of 25° C.±15° C., but is not limited thereto. Specifically, the pH of the acidic solution may be in the range of pH 2 to pH 6.9, more specifically, pH 3 to pH 6.5, and even more specifically, pH 4 to pH 6, but is not limited thereto.

In an exemplary embodiment of the present invention, a foreign target material was introduced into a cell through a cracked membrane while maintaining the activity and genetic information of the binding protein displayed on the inclusion bodies in the cell, by freezing E. coli cells at −20° C., thawing at 37° C., and increasing the permeability of the cell membrane or cell wall by treating with an acid solution or chelating agent (Example 5).

Additionally, in the present invention, step (c) may further include introducing a competitive binding protein into a cell along with a target material; or introducing a competitive binding protein into a cell after the occurrence of an interaction between the binding protein displayed on the inclusion bodies and the target material. Since the introduction of other binding protein(s), which competes with the binding protein displayed on the active inclusion bodies for the target material, into a cell reduces the fluorescence intensity of the cell interacted conjugated to the target material, improved affinity binding proteins can be screened based on the same. In the present invention, the screening method using the competitive binding proteins can be used interchangeably with the screening for affinity maturation of binding proteins.

The competitive protein is not limited as long as it can compete with the binding protein displayed on the active inclusion bodies for the same target material, and the competitive protein may be a protein or material which is the same as or different from the binding protein displayed on the active inclusion bodies.

In an exemplary embodiment of the present invention, a library for affinity maturation was constructed using a H2 protein, which is a binding protein that binds to sfGFP according to the intracellular particle display technology of the present invention (FIG. 20). After selecting H2C1

(Kd=518 nM), which is a binding protein with matured affinity, via competitive screening by adding H2 repebody as a competitor and using the above library (b of FIG. 19 and FIGS. 20 and 21), a competitive screening was performed by treating the same library with H2C1 protein as a competitor. As a result, H2C13 (Kd=17.3 nM), which is a binding protein whose affinity is improved 159-fold compared to that of the existing H2 protein, was successfully isolated (FIGS. 20 and 21).

As used herein, the term "a fluorescent material" refers to a material which reacts to a particular energy level or spontaneously emits fluorescence. In the present invention, it may be used to refer to a fluorescent protein and a fluorescent compound. As used herein, the term "fluorescent protein" may refer to a polypeptide which reacts to a particular energy level or spontaneously emits fluorescence, and may be selected from the group consisting of green fluorescent protein (GFP), enhanced green fluorescent protein (EGFP), modified green fluorescent protein (mGFP), red fluorescent protein (RFP), monomeric red fluorescent protein (mRFP), enhanced red fluorescent protein (ERFP), *Discosoma* sp. red fluorescent protein (DsRed), blue fluorescent protein (BFP), enhanced blue fluorescent protein (EBFP), cyan fluorescent protein (CFP), cyan green fluorescent protein (CGFP), enhanced cyan fluorescent protein (ECFP), yellow fluorescent protein (YFP), enhanced yellow fluorescent protein (EYFP), azami green (AzG), *Heteractis crispa* red fluorescent protein (HcRed), and blue fluorescent protein (BFP), but is not limited thereto. Additionally, the fluorescent compound may refer to a fluorophore which can modify a target material, and may be one selected from the group consisting of the fluorescent protein; a xanthene derivative (fluorescein, rhodamine, Oregon green, eosin, and Texas red); a cyanine derivative (cyanine, indocarbocyanine, oxacarbocyanine, thiacarbocyanine, and merocyanine); a naphthalene derivative (dansyl and prodan derivatives); a coumarin derivative; an oxadiazole derivative (pyridyloxazole, nitrobenzoxadiazole, and benzoxadiazole); a pyrene derivative (cascade blue); an oxazine derivative (Nile red, Nile blue, cresyl violet, and oxazine 170); an acridine derivative (proflavin, acridine orange, and acridine yellow); an arylmethine derivative (auramine, crystal violet, and malachite green); and a tetrapyrrole derivative (porphin, phthalocyanine, and bilirubin); but is not limited thereto.

In the present invention, the fluorescent protein, which forms a fusion protein with a binding protein, and the fluorescent material, which modifies a target material, may have fluorescence with different wavelengths. Specifically, they may differ in the wavelengths of the fluorescent signals emitted by each so that a fluorescent signal detector can detect each signal by distinguishing based on the difference.

In the present invention, the binding protein may or may not include a fluorescent protein; however, the target material must include the fluorescent protein or fluorescent material.

In an exemplary embodiment, plasmids pInVLR5c-mRFP-CBD and pD3E8-mRFP-CBD, which encode binding proteins, included RFP as a fluorescent protein, and in the case of the target protein, IL6, GFP was included as a fluorescent protein.

As used herein, the term "a fluorescent signal" refers to the wavelength of an energy caused by a fluorescent protein or a fluorescent material, and it may be expressed in values using a fluorescent signal detector.

The measurement of an intracellular fluorescent signal is performed using a fluorescent microscope or flow cytometer. In an exemplary embodiment, the fluorescence of GFP and RFP was analyzed by detecting at FL1 (530/30 nm) and FL2 (585/42 nm) PMT using flow cytometer FACS Calibur (BD Biosciences, CA, USA), respectively. The inclusion body cell (PPI+), in which pD3E8-mRFP-CBD having a binding affinity for IL6 (a target material) is expressed, and the inclusion body cell (PPI−), in which pInVLR5c-mRFP-CBD having no binding affinity for IL6 (a target material) is expressed, were respectively introduced into cells with IL6 protein, which was connected to GFP by the optimized method of increasing cell permeability. The difference in binding affinity for IL6 was confirmed by GFP fluorescence (FIG. 11). Comparing with the result obtained by the existing method, where a bait protein and a binding material are simultaneously expressed in a cell (Korean Patent Application Publication No. 10-2013-0023057), the existing method is to analyze the interactions between proteins using the difference between localization and dispersion of fluorescent signals, which are conjugated to binding materials on the intracellular inclusion bodies, according to the presence/absence of an interaction with the bait protein and the binding material. In contrast, the method of the present invention is to measure the intensity of the fluorescent signal of a target material, which is bound to a binding protein by an interaction after the target material is introduced from the outside into a cell by the optimized method of increasing cell permeability. Accordingly, the method of the present invention showed a distinctive result with a 450-fold or higher difference in the signal-to-noise ratio while the existing method showed a negligible difference of an about 2-fold in the signal-to-noise ratio (FIG. 13).

In an exemplary embodiment of the present invention, D3E8 and InVLR5c were used as binding proteins, CBD proteins of family II derived from *Cellulomonas fimi* as active inclusion bodies, and IL6 as a target protein. However, the present invention is not limited thereto, and it should be obvious to one of ordinary skill in the art that any kind of binding proteins, target materials, and active inclusion bodies may be applied for the analysis of the interactions between the binding protein and the target material.

The method of the present invention may further include (e) recovering a fusion protein present in the recovered cells by an individual cell unit; or isolating the gene encoding the fusion protein or a binding protein after step (d). The gene isolation may further include amplifying the isolated gene. The recovery of the protein; and isolation and amplification of the gene may be performed by a method widely used in the art.

As used herein, the term "recovery" refers to a process of selecting only those cells in which the interaction between the binding protein and the target material was confirmed after measuring the fluorescent signal of a fluorescent material conjugated to a target material from a cell library including a binding protein. The flow cytometer may be a device capable of measuring a cell size, an intracellular composition, and intensity of fluorescence, and specifically, a device capable of isolating and recovering single cells according to the cell size, intracellular composition, and intensity of fluorescence desired by the experimenter.

As used herein, the term "isolation" refers to a process of isolating a polynucleotide encoding a binding protein from a cell when the cell, which was confirmed to have an interaction between the binding protein and a target material, was recovered from a cell library including the binding protein. The isolation may refer to an isolation of DNA from a cell. The DNA isolation may be performed by any method known in the art as long as it does not run counter to the object of isolating the polynucleotide encoding the binding protein.

As used herein, the term "amplification" refers to a process of increasing the polynucleotide encoding the binding protein isolated above in a large amount using the general polynucleotide amplification method known in the art. The amplification method may be selected according to the use of the amplified polynucleotide, and the selection can be easily made by one of ordinary skill in the art.

In an exemplary embodiment of the present invention, it was examined whether the difference according to the presence/absence of binding affinity can be analyzed by a high-throughput flow cytometer using the difference in fluorescence intensity of GFP conjugated to a target material according to the interaction between a binding protein displayed on the inclusion bodies and a target material. A library-like environment was manipulated by mixing the IT cells (in which D3E8 (PPI+), an LRR protein having a binding affinity for IL6 of about 2 nM, was displayed on the inclusion bodies), the IT cells (in which F11 (PPI+), an LRR protein having a binding affinity for IL6 of about 117 nM, was displayed on the inclusion bodies), and the IT cells (in which InVLR5c (PPI−) was displayed on the inclusion bodies) in a 1:10:10000 ratio, respectively; and 10,000 E. coli cells having high affinity for IL6 were recovered using a flow cytometer (FACSaria) from the sample, which was subjected to the process of increasing permeability and to which protein interaction was induced. Plasmids were purely isolated from the recovered cells and then transformed into DH5a E. coli cells. The thus-formed colonies were subjected to PCR amplification and the presence of gene recovery of the cells recovered based on the phenotype (D3E8-mRFP-CBD protein) was examined (FIG. 14).

In still another aspect, the present invention provides a method for screening and/or preparing a binding protein specific to a target material, including isolating a gene encoding a binding protein specific to a target material present in the cell recovered by the screening method of the present invention. Since the cell recovered according to the screening method of the present invention contains a gene encoding the binding protein specific to a target material, a binding protein specific to a target material can be screened and/or prepared by isolating and/or analyzing the gene from the recovered cell.

The gene isolation may further include amplifying the isolated gene. The recovery of the protein or the isolation and amplification of the gene may be performed using a method widely used in the art.

Since the method of the present invention employs a binding protein which was overexpressed in a cell and conjugated into the inclusion bodies, the level of signal intensity is a few hundred to a few hundred thousand times higher than the fluorescent signal obtained by the existing cell surface expression. Therefore, the method of the present invention, based on the result, can be used in various kinds of protein engineering including the protein library screening, which includes a fractionation into an individual cell unit.

In another aspect, the present invention provides a method for analyzing the interaction between a binding protein and a target material, including (a) providing a cell library comprising a construct, which comprises a polynucleotide encoding a fusion protein consisting of a binding protein and an active inclusion body protein; (b) expressing the fusion protein in the cell library, thereby forming interaction trapper (IT) cells, wherein the binding protein is displayed on the inclusion body; (c) introducing a fluorescence material-conjugated target material into the cells according to step (b); and (d) measuring the interaction between the binding protein and the target material based on the fluorescence intensity of the fluorescence material conjugated to the target material.

In an exemplary embodiment of the present invention, the process of increasing cell permeability was performed by a method including: centrifuging the cells in step (b), in which the binding protein was expressed, to form a pellet followed by freezing at −20° C.; and thawing the pellet at 37° C. and treating with an acid solution, specifically, with 0.1 M citric acid (pH 4).

As used herein, the term "microorganism" refers to all kinds of cells that can express a fusion protein, which consists of a binding protein and an active inclusion body protein of the present invention, thereby displaying the fusion proteins in the intracellular inclusion bodies. The microorganism may be a eukaryotic or prokaryotic cell, but is not limited thereto, and it may be, for example, E. coli.

Since the existing technology of increasing cell permeability aims at the cell permeability itself for obtaining protein and genetic information by extracellular release of the intracellular proteins and genetic information, it intends to perfectly release the intracellular proteins and genetic information by increasing cell permeability. However, the present inventors have made efforts to establish a process of increasing cell permeability that enables a smooth introduction of a target material into a cell without affecting the activity and genetic information of the binding protein, which is displayed on the active inclusion bodies. As a result, they have successfully established the process of increasing cell permeability of the present invention.

Accordingly, the method of increasing cell permeability in a microorganism membrane according to the present invention has novel effects of being capable of stably maintaining the activity and genetic information of the binding protein displayed on the intracellular inclusion body of a microorganism, and introducing a foreign target material into a cell while maintaining the shape of the cell.

In an exemplary embodiment of the present invention, the process of increasing cell permeability was performed by a method including: centrifuging the microorganism (E. coli) to form a pellet followed by freezing at −20° C.; thawing the pellet at 37° C. and treating with an acid solution, specifically, with 0.1 M citric acid (pH 4). As such, the external target protein formed IT cells, which were increased with respect to their cell permeability that enabled the free introduction of the external target material into the cell, and it was confirmed that the use of the IT cells enabled the measurement of interactions between proteins with high sensitivity, thereby making it possible to obtain genetic information.

In still another aspect, the present invention provides a cell including a construct, which contains a polynucleotide encoding a fusion protein consisting of a binding protein and an active inclusion body protein.

The binding protein, active inclusion body protein, fusion protein, and cell are the same as explained above.

In an exemplary embodiment of the present invention, the LRR protein was used as a binding protein, the CBD protein as an active inclusion body protein, and the IL6 protein as a target material, and IT cells were formed by transformation of a polynucleotide encoding a fusion protein between the binding protein and the CBD protein into an E. coli cell.

In still another aspect, the present invention provides a cell library including a construct, which includes a polynucleotide encoding a fusion protein consisting of a binding protein and an active inclusion body protein. The library may be a DNA library or cell library transformed therewith.

The binding protein, active inclusion body protein, fusion protein, and cell are the same as explained above.

As used herein, the term "cell library" refers to a library consisting of cells which include plasmids encoded by binding proteins interacting with target materials, and specifically, a library consisting of cells in which binding proteins are stably displayed in inclusion bodies and target materials can be introduced into cells. The cell library specifically consists of *E. coli* cells, but is not limited thereto.

In an exemplary embodiment of the present invention, the manipulated mimic library was used, having been prepared by mixing the cells of D3E8 (PPI+) [an LRR protein having an affinity for IL6 (i.e., a target material) of about 2 nM], F11 (PPI+) [an LRR protein having an affinity for IL6 of about 117 nM], and InVLR5c (PPI−) [an LRR protein having no affinity for IL6], which were respectively displayed on the inclusion bodies, in a 1:10:10000 ratio. In another exemplary embodiment of the present invention, a random library was constructed on repebody (LRR protein) for screening using an intracellular particle display system and used as a real library.

In still another aspect, the present invention provides IT cells, where the fusion protein consisting of a binding protein and an active inclusion body protein is expressed and the binding protein is displayed on the inclusion body, and a cell library thereof.

The binding protein, active inclusion body protein, fusion protein, cell, and cell library are the same as explained above.

MODES FOR CARRYING OUT THE INVENTION

Hereinbelow, the present invention will be described in detail with accompanying examples. However, the examples disclosed herein are only for illustrative purposes and should not be construed as limiting the scope of the present invention.

Example 1: Acquirement of Genes and Enzymes

A cellulose-binding domain (CBD, SEQ ID NO: 15) gene of family II was cloned using the exoglucanase gene of *Cellulomonas fimi* KCTC 9143 strain obtained from the Korean Collection of Type Cultures (KCTC). The improved modified green fluorescent protein (mGFP, SEQ ID NO: 16) gene was obtained from the pEGFP (Clontech, CA, USA), a commercial vector, and the plasmid vector pRFP including the mRFP1 (monomeric red fluorescent protein 1, SEQ ID NO: 17) gene was provided by the Korea Advanced Institute of Science and Technology (KAIST) (Daejeon, Korea). Among the repebody (InB-VLR) family (artificial antibody protein), which is an artificial protein where the N-terminus of internaline B (InB) protein, a modified repeat module of a variable lymphocyte receptor (VLR) protein, and the C-terminus of VLR protein are conjugated, In-VLR5c (Korean Patent Application Publication No. 10-2010-0086055, SEQ ID NO: 18), which has no binding affinity for IL6; and In-VLR5c-D3E8 (SEQ ID NO: 19, KD=2 nM) and In-VLR5c-F11 (SEQ ID NO: 20, KD=117 nM), which have binding affinity for IL-6, were used. Human interleukin-6 (hIL-6) is a vector in which the gene of hIL-6 (SEQ ID NO: 21) is cloned therein. All of the above genes were provided by the KAIST (Daejeon, Korea) and all of the enzymes used in the present invention were purchased from New England Biolabs (NEB, England).

Example 2: Construction of a Recombinant Vector

All of the primers used in the present invention were synthesized by Bioneer Corporation (Daejeon, Korea). The primers are shown in Table 1 below. The restriction sites such as NdeI and KpnI are indicated in bold in Table 1. All genes used in the present invention were amplified using each of the primers shown in Table 1, conjugated by overlap extension PCR, inserted into the NdeI and HindIII restriction sites of pET21a vector, and recombined using *E. coli* DH5a cells. The thus-prepared plasmid vectors were designated as pInVLR5c-mRFP-CBD, pD3E8-mRFP-CBD, pF11-mRFP-CBD, pGFP-IL6, respectively. Additionally, the pInVLR5c-mRFP-CBD plasmid, after treating with the restriction enzymes of NdeI and HindIII, was inserted into the pET21a vector, which was treated with NdeI and HindIII, and recombined using *E. coli* DH5a cells. The thus-prepared plasmid vector was designated as pInVLR5c-mRFP.

TABLE 1

| Primer Name | Sequence (5'→3') | SEQ ID NO |
|---|---|---|
| ndeI histag VLR F | GGAATTCCATATGGGCAGCAGCCACCACCACCACC ACCACAGCAGCGGCGGATCCGAAACCATTACCGTG AGCACCCC | 1 |
| gs linker D3E8 R | GGACCCAGAGCCGCTACCGGTACCGGTCGGGCAAA TAATGCTACGC | 2 |
| gs linker mRFP F | GGTAGCGGCTCTGGGTCCATGGCCTCCTCCGAGGAC G | 3 |
| pt linker mRFP R | TCGGAGGGAATTCACCGGAACCGCGTGGCACCAGA CCGGCGCCGGTGGAGTGGC | 4 |
| pt linker cex F | TTCCGGTGAATTCCCTCCGACGCCGACCCCGACTAG TGGTCCGGCCGGGTG | 5 |
| HindIII CBD R | CCCCCCAAGCTTTAGCCGACCGTGCAGGGCG | 6 |
| gs linker InVLR5c R | GGACCCAGAGCCGCTACCGGTACCAACTTCCAGGG TCGGACAGATAATG | 7 |

TABLE 1-continued

| Primer Name | Sequence (5'→3') | SEQ ID NO |
|---|---|---|
| ndeI histag mGFP F | GGAATTCCATATGGGCAGCAGCCACCACCACCACC ACCACAGCAGCGGCGGATCCGTGAGCAAGGGCGAG GAGCTG | 8 |
| gs linker mGFP R | GGACCCAGAGCCGCTACCCTTGTACAGCTCGTCCAT GCCGA | 9 |
| gs linker IL6 F | GGTAGCGGCTCTGGGTCCGAATTCGCCCCAGTACCC CCAGGAGAAG | 10 |
| HindIII IL6 R | CCCCCCAAGCTTTTACATTTGCCGAAGAGCCCTCAG G | 11 |
| D3E8 specific F | GCAGCTGTGGGCGAATCAAC | 12 |
| InVLR5c specific F | GACGTATCTGATTCTGACCGGT | 13 |
| mRFP R | GAAGCGCATGAACTCCTTGATG | 14 |

In-VLR5c-D3E8 and In-VLR5c-F11 genes were amplified using primer 1 (SEQ ID NO: 1) and primer 2 (SEQ ID NO: 2) and In-VLR5c gene was amplified using primer 1 (SEQ ID NO: 1) and primer 7 (SEQ ID NO: 7) from each of the vectors where In-VLR5c-D3E8, In-VLR5c-F11, and In-VLR5c genes were cloned, respectively. mRFP1 gene was amplified from a vector where mRFP1 gene was cloned using primer 3 (SEQ ID NO: 3) and primer 4 (SEQ ID NO: 4) and GFP gene was amplified from pEGFP gene using primer 8 (SEQ ID NO: 8) and primer 9 (SEQ ID NO: 9). CBD gene was amplified from CBD using primer 5 (SEQ ID NO: 5) and primer 6 (SEQ ID NO: 6) (see *J Microbiol Biotechnol.* 2008 March; 18 (3): 443-8) and hIL6 gene was amplified from a vector where hIL6 gene was cloned using primer 10 (SEQ ID NO: 10) and primer 11 (SEQ ID NO: 11).

Example 3: Plasmid Isolation

The pInVLR5c-mRFP-CBD, pD3E8-mRFP-CBD, pF11-mRFP-CBD, and pInVLR5c-mRFP plasmids prepared in Example 2 were transformed into *E. coli* DH5α, inoculated into LB medium (1% bacto-trypton, 0.5% yeast extract, and 1% NaCl) containing ampicillin (50 μg/mL), and incubated in a shaking incubator at 37° C. for 24 hours. The cultured cell suspension was centrifuged at 4,470×g for 5 minutes using a centrifuge (Universal 320R, Hettich), and the plasmids were isolated from the pellet freed from the supernatant using the QIAprep® spin miniprep kit, and the isolated plasmids were confirmed on a 1% agarose gel by electrophoresis.

Additionally, the pGFP-IL6 plasmid prepared in Example 2 was transformed into *E. coli* DH5α, inoculated into LB medium (1% bacto-trypton, 0.5% yeast extract, and 1% NaCl) containing ampicillin (50 μg/mL), and incubated in a shaking incubator at 37° C. for 24 hours. The cultured cell suspension was centrifuged at 4,470×g for 5 minutes using a centrifuge (Universal 320R, Hettich), and the plasmids were isolated from the pellet freed from the supernatant using the QIAprep® Spin Miniprep Kit, and the size and nucleotide sequences of the isolated plasmids were confirmed on a 1% agarose gel by electrophoresis followed by sequencing analysis.

Example 4: Expression and Purification of Proteins

The pD3E8-mRFP-CBD, pInVLR5c-mRFP-CBD and pInVLR5c-mRFP plasmids prepared in Example 2 were transformed into *E. coli* BL21 (DE3), inoculated into LB medium (1% bacto-trypton, 0.5% yeast extract, and 1% NaCl) containing ampicillin (50 μg/mL), and incubated in a shaking incubator at 37° C. When the optical density at 600 nm reached 0.5, isopropyl-1-thio-β-D-galactopyranoside (IPTG; 200 μM) was added to the culture to induce the CBD inclusion bodies and cultured at 30° C. for 5 hours. The presence of proteins and protein inclusion bodies formed in the cultured cells was confirmed using a fluorescence microscope (ZEISS) (FIG. 3).

The pGFP-IL6 plasmid was transformed into *E. coli* OrigamiB (DE3), inoculated into LB medium (1% bacto-trypton, 0.5% yeast extract, and 1% NaCl) containing ampicillin (50 μg/mL), and incubated in a shaking incubator at 37° C. When the optical density at 600 nm reached 0.5, isopropyl-1-thio-β-D-galactopyranoside (IPTG; 200 μM) was added to the culture to express hIL6 protein and cultured at 30° C. for 5 hours. The expression of GFP-hIL6 protein in the cultured cells was confirmed using a fluorescence microscope. The culture of the cells, in which the expression of the fusion protein was confirmed, was subjected to ultrasonication on ice to crush cell membranes, and the lysed cells were again separated by centrifugation at 20,000×g for 20 minutes to remove precipitates, and only the supernatant was filtrated with a 0.2 μm filter and subjected to a subsequent purification process. The protein was purified using the HiTrap™ Q HP (GE Healthcare, Uppsala, Sweden), which is an affinity chromatography column connected to the fast-performance liquid chromatography (FPLC), using 6× His-tag expressed on the N-terminus of GFP-hIL6, desalted with PBS buffer (pH 7.4), concentrated at a concentration of 40 mg/mL using a centrifugal filter (Sartorius Stedim Biotech), and stored at −20° C. for use in Examples described below. The purified GFP-hIL6 protein was analyzed by SDS-PAGE.

Example 5: Increase of Permeability of IT Cells

For the introduction of a foreign target material into the pD3E8-mRFP-CBD cells or pInVLR5c-mRFP-CBD cells cultured in Example 4, the optimized method of increasing cell permeability developed in the present invention was performed. The *E. coli* cell culture was centrifuged at 2,480×g for 5 minutes, and the pellet was frozen at −20° C. The frozen *E. coli* cells were thawed by PBS buffer (pH 7.4) at 37° C., centrifuged at 2,480×g for 5 minutes, and the supernatant was removed. The resulting *E. coli* cells were treated with 0.1 M citric acid (pH 4), centrifuged to remove the supernatant, and resuspended with PBS buffer (pH 7.4).

Example 6: Analysis of Genes in Cracked Cells According to the Presence of Display of Inclusion Bodies The permeability of pInVLR5c-mRFP-CBD cells cultured in Example 4 was increased in the same manner as in Example 5, centrifuged at 4,470×g for 5 minutes using a centrifuge (Universal 320R, Hettich) and divided into a cell supernatant and a pellet. The pellet was resuspended with PBS buffer (pH 7.4) in an equal amount to that of the cell supernatant. The cell supernatant and the pellet resuspension were respectively mixed with the iQTM SYBR® Green supermix (Bio-rad) in a 1:1 ratio, respectively treated with 10 pmol of primer 13 (SEQ ID NO: 13) and primer 14 (SEQ ID NO: 14), and the amount of DNA was analyzed using the CFX96 (Bio-rad), a quantitative PCR instrument.

Example 7: Construction of a Protein Structure-Based Library of Binding Proteins For the construction of a library of repebody, which is an LRR protein used as a model binding protein, the method used in Korean Patent No. 10-1356075 was applied in the same manner. Six amino acid residues at positions 126, 128, 129, 150, 152, and 153 located at the concave region of two mutation modules (LRRV modules 3 and 4) were selected using repebody. Then, the selected amino acids were substituted with an NNK degenerate codon and thereby synthesized mutagenic primers for library construction. Subsequently, overlap PCR was performed with respect to the two modules using the primers to obtain library DNA, and a library gene was substituted and inserted on the position of the InVLR5c gene of the recombined vector, pInVLR5c-mRFP-CBD, thereby securing the library plasmid connected to the mRFP-CBD gene. Thus the secured library was introduced into *E. coli* DH5a by electroporation to obtain transformants, thereby constructing a library with a variety at $1 \times 10^7$ level.

Example 8: Construction and Expression of an Expression Library Displayed on Active Inclusion Bodies The library colonies prepared in Example 7 were recovered using storage buffer (2xTY medium, 50% glycerol, 20% glucose) and centrifuged at 4,470×g for 5 minutes. After discarding the supernatant, library plasmids were isolated from the pellet using the QIAprep® Spin Miniprep Kit. The isolated library plasmids (1 µg) were transformed into *E. coli* BL21 (DE3) by electroporation and thereby an expression library with a variety at $1 \times 10^7$ level was constructed. The expression library colonies were recovered with storage buffer and the cells with the $OD_{600}$ value of 0.05 were collected, inoculated into LB medium (1% bacto-trypton, 0.5% yeast extract, and 1% NaCl) containing ampicillin (50 µg/mL), and grown in a shaking incubator at 37° C. When the $OD_{600}$ value reached 0.5, the culture was treated with 200 µM IPTG to induce CBD inclusion bodies and cultured at 30° C. for 3 hours. The cultured cells were centrifuged and the supernatant was discarded, and the pellet was frozen at −20° C.

Example 9: Analysis of Interactions Between Proteins by a Flow Cytometer

The IT cell suspensions, in which pD3E8-mRFP-CBD (PPI+) or pInVLR5c-mRFP-CBD (PPI−) which underwent a process of increasing cell permeability was expressed, were respectively treated with GFP-IL6 protein (10 µM) purified and isolated in Example 4, stirred for 30 minutes for introducing a foreign target material into cells, thereby inducing an interaction between proteins. 30 minutes thereafter, the cells were washed with PBST, PBS buffer (pH 7.4) and the interaction between the binding protein and the target material was analyzed by a fluorescence microscope (A of FIG. 13) or a flow cytometer (B of FIG. 13). Flow cytometry was performed using the FACS Calibur (BD Biosciences, CA, USA) and the analysis gate was set based on SSC and FSC parameters. GFP and RFP fluorescence were detected with FL1 (530/30 nm) and FL2 (585/42 nm) PMT, respectively; the compensation was set in a ratio (FL1-FL2:FL2-FL1=16%:16%); and 10,000 events were counted in each sample. Data was collected using the BD CellQuest Pro (version 4.0.2, 145 BD Biosciences) software and analyzed using the Flowjo software (version 10).

Example 10: Library Screening by Intracellular Particle Display

After increasing the cell permeability of the frozen pellet prepared in Example 8 by the method of Example 5, various kinds of targets (mGFP-IL6, sfGFP. Fluorescein, and dextran-FITC) conjugated to GFP were induced to have an interaction with the inclusion bodies, in which a binding protein library is displayed, respectively, and the interacting cells were recovered. The interacting cells were sorted using the FACSaria™ III (BD Biosciences, CA, USA) and the analysis gate was set based on SSC and FSC parameters. GFP and RFP fluorescence were detected with FL1 (530/30 nm) and FL2 (585/42 nm) PMT, respectively; the compensation was set in a ratio (PE-FITC:FITC-PE=28.62:4.29); and 10,000 events were counted in each sample. Data was collected using the BD FACS Diva (version 7.0 BD Biosciences) software and analyzed using the Flowjo software (version 10).

Example 11: Analysis by Electron Microscopes (SEM, TEM)

*E. coli* cells that underwent the treatment of Example 5 were pre-fixed in a paraformaldehyde-glutaraldehyde fixative (4° C., phosphate buffer, pH 7.2) for 2 hours, washed 3 times with phosphate buffer (0.1 M, pH 7.2) for 10 minutes per wash, and post-fixed in 1% $OsO_4$ (25° C., 0.1 M phosphate buffer, pH 7.2) for 2 hours. The materials, upon completion of fixation, were washed several times with the same buffer, dehydrated with an increasing concentration of ethanol, substituted with isoamyl acetate, dried using a critical point dryer, coated to a thickness of 20 nm using the SC502 sputter coater, and observed using the FEI Quanta 250 FEG (FEI, USA) scanning electron microscope (SEM), installed in the facility of Korea Research Institute of Bioscience and Biotechnology (KRIBB), at 10 kV.

For the observation by a transmission electron microscope, the cut-off part was pre-fixed in a paraformaldehyde-glutaraldehyde fixative (4° C., phosphate buffer, pH 7.2) for 2 hours, washed 3 times with phosphate buffer (0.1 M, pH 7.2) for 10 minutes per wash, and post-fixed in 1% OsO4 (25° C., 0.1 M phosphate buffer, pH 7.2) for 2 hours. The materials, upon completion of fixation, were washed several times with the same buffer, dehydrated with an increasing concentration of ethanol, substituted with propylene oxide, dried using a critical point dryer, coated to a thickness of 20 nm using the SC502 sputter coater, embedded with Epon-812, and polymerized in a 60° C. oven for 36 hours. The embedded tissue was prepared into ultrathin sections using the ultra-microtome (ULTRACUT E, Leica Microsystems, Australia), double-stained with uranyl acetate and lead citrate, and observed using the transmission electron microscope (TEM, CM 20, Philips, the Netherlands), at 10 kV.

Example 12: Display of a Binding Protein on Inclusion Bodies

In order to confirm that the CBD inclusion bodies are active inclusion bodies capable of stably maintaining the activity and expression of displayed binding proteins, VLR (InVLR5c), which is a binding protein, and mRFP, which is a fluorescent protein, were conjugated to a CBD tag and overexpressed in E. coli, thereby forming inclusion body cells. The inclusion bodies were separated alone by ultrasonication and examined by a fluorescence microscope. The fluorescence of mRFP, a fluorescent protein, was observed in the location of inclusion bodies, thus confirming that the binding proteins such as VLR and mRFP were displayed on the CBD inclusion bodies. The fluorescence of mRFP was also observed in the inclusion bodies separated by ultrasonication, thus confirming that the CBD inclusion bodies can stably display binding proteins while maintaining the activity of the binding proteins (FIG. 3).

Example 13: Effect of Increasing Cell Permeability on Inside/Outside of Cells

In order to confirm the effect of the process of increasing cell permeability developed in the present invention on cells, experiments were performed using the VLR-mRFP-CBD cell, in which a binding protein and an RFP protein are displayed on the inclusion bodies, and the VLR-mRFP cells, in which a binding protein and an RFP fusion proteins are not displayed. A two-step process of increasing cell permeability (freezing/thawing and acid solution treatment) was performed using the VLR-mRFP-CBD cell, in which a binding protein was displayed on active inclusion bodies, and the VLR-mRFP cell without inclusion bodies, and the differences between the two different cells were observed using a flow cytometer and a fluorescence microscope.

The intracellular changes according to the presence/absence of inclusion bodies after freezing and thawing during the process of increasing cell permeability were analyzed using a flow cytometer and fluorescent images (FIG. 4). As a result, it was confirmed that when binding proteins were displayed on the active inclusion bodies, the binding proteins stably maintained their expression in the cell even after the freezing/thawing process, whereas when the binding proteins were not displayed on the inclusion bodies, most of the binding proteins were lost in the cell. These results show that the freezing/thawing process increased the permeability of the cell wall, thereby releasing intracellular molecules to the outside of the cell, whereas when binding proteins were stably displayed on the inclusion bodies they remained in the cell without being lost to the outside of the cell.

Additionally, regarding the introduction of a foreign target material into a cell, it was confirmed that although the intracellular introduction cannot be achieved by the freezing/thawing process alone (FIG. 5), the intracellular introduction can be made possible when the inclusion body cell that underwent the freezing/thawing process is treated with an acid solution or EDTA, a chelating agent (FIG. 6). As illustrated in FIG. 6, it was confirmed that the most effective method for the intracellular introduction of a foreign target material is to treat with 0.1 M citric acid (pH 4), thereby completing the optimized membrane treatment of the present invention.

The interaction between a foreign target material and a binding protein, which moves to the inside of a cell and becomes displayed on the inclusion bodies, was observed in fluorescent images through the optimized process of increasing cell permeability (A of FIG. 7). As a result of flow cytometry, where a target material moves to the inside of a cell within a short period of time (1 minute) and interacts with a binding protein (B of FIG. 7), it was confirmed that the cracked cell membrane was in a state that the target material can easily move.

FIG. 8 shows the result confirming that the interaction between an external target material, which is introduced into the inside of a cell through the optimized process of increasing cell permeability, and a binding protein, which is displayed on the inclusion bodies, is not a non-specific interaction but a specific interaction that occurs based on the degree of affinity for the target material, in a state maintaining the endogenous activity of the binding protein.

In order to confirm the maintenance of genetic information of a binding protein according to the presence/absence of the display of the active inclusion body, the VLR-mRFP-CBD cell, where the binding protein is displayed on the inclusion body, and the VLR-mRFP cell without inclusion bodies were respectively separated into a pellet and a supernatant by the optimized process of increasing cell permeability developed in the present invention. Then, the presence/absence of the plasmid, which possesses the genetic information of the binding protein between two different cells according to the process of increasing cell permeability, was confirmed by quantitative PCR (Q-PCR). As a result, it was confirmed that most of the genetic information of the binding protein displayed on the active inclusion body was stably maintained while the genetic information of the binding protein not displayed on the active inclusion body was lost to the outside of the cell (FIG. 10).

Example 14: Validation of an Intracellular Particle Display System

In order to validate the intracellular particle display technology by the optimized process of increasing cell permeability developed in the present invention, experiments were performed using a model binding protein and a model target material. FIG. 11a shows data that a foreign target material can be introduced into the inside of a cell only after the two-step process of increasing cell permeability developed in the present invention, and the introduced target material can be co-localized into the inclusion bodies by interacting with the binding protein displayed on the inclusion body.

FIG. 11b shows an experiment for confirming the maintenance of genetic information in a cell after the process of increasing cell permeability. Specifically, the repebody-mRFP-CBD cell, in which a binding protein is displayed into the active inclusion bodies, was separated into a pellet and a supernatant, respectively, by the process of increasing cell permeability developed in the present invention, and the pellet was resuspended with an equal amount of PBS buffer (pH 7.4). The presence/absence of the plasmid possessing the genetic information of the binding protein was confirmed by quantitative PCR (Q-PCR) using the pellet suspension and the supernatant. Additionally, the intracellular plasmid before and after the process of increasing cell permeability was isolated and confirmed by electrophoresis. As a result, it was confirmed that the genetic information of the binding protein displayed on the active inclusion bodies was stably maintained in the cell regardless of the process of increasing cell permeability.

This result confirms that the present invention is a system enabling a protein library screening, which includes: fractionating into an individual cell unit using the interaction between a binding protein and a target material, due to the characteristics that the binding protein is displayed on the intracellular active inclusion bodies and that the genetic information of the binding protein is maintained due to the process of increasing cell permeability; and recovering the genetic information in the individual cell unit.

FIG. 11c shows the result of the cell shape before and after the process of increasing cell permeability confirmed by a flow cytometer and an electron microscope, which confirmed that the cell shape was stably maintained even after the process of increasing cell permeability.

That is, the result supports that the process of increasing cell permeability developed in the present invention is a unique method distinctively different from other existing methods of increasing cell permeability, which can stably introduce external target materials into cells by increasing the permeability of cell walls and cell membranes without destroying the cells, while stably maintaining the binding proteins displayed on the active inclusion bodies and the genetic information thereof simultaneously.

FIG. 12 shows the results of an experiment which confirmed the size of a target material that can be introduced by the optimized process of increasing cell permeability, in which interaction trapper cells, where the C20 (PPI+) (a dextran-FITC binding protein obtained from a screening using an intracellular particle display system) and a binding protein (negative control, which does not bind to dextran-FITC) were displayed on the inclusion bodies, were used. After treating each cell (PPI+ and PPI−) with a process of increasing cell permeability, dextran-FITC at various sizes (molecular weight of 3,000 to 5,000; 70,000; and 250,000) was introduced into the cells to induce interactions. As a result, it was confirmed that the dextran-FITC with a molecular weight of 250,000 was approved into cells, thereby interacting with the binding proteins displayed on the intracellular inclusion bodies, and this confirms that the process of increasing cell permeability of the present invention can easily introduce even macromolecules into cells, and a protein binder can be obtained via library screening by inducing an interaction using the macromolecules as targets.

Example 15: Analysis of Protein Interactions Using an Intracellular Particle Display Technique In order to confirm the interactions between proteins by intracellular particle display using the optimized process of increasing cell permeability in Examples above, D3E8 (Kd=2 nM, which has an affinity for IL6), and the InVLR5c protein (which has no affinity for IL6) were used as model binding proteins and displayed on the inclusion bodies, respectively. The pD3E8-mRFP-CBD and pInVLR5c-mRFP-CBD plasmids were transformed into *E. coli* and their fusion proteins were expressed, respectively. GFP-IL6 protein, a target material, was introduced into cells by the optimized process of increasing cell permeability of Example 5, and then the cells were observed using a fluorescence microscope and a flow cytometer.

As a result, it was observed that the GFP-IL6 fluorescence was co-localized with the RFP fluorescence displayed on the intracellular inclusion bodies along with the binding proteins in the inclusion body cells (PPI+), in which the pD3E8-mRFP-CBD having an affinity for IL6 was expressed, whereas, in the pInVLR5c-mRFP-CBD (PPI−) cells, in which the LRR protein having no affinity for IL6 was expressed, the GFP fluorescence of the binding proteins was not observed at all but only the RFP fluorescence of the binding proteins was observed (A of FIG. 13). That is, the presence of interactions between proteins was apparently confirmed based on the fluorescence intensity of target materials bound to the binding proteins via interactions. In short, these results support that the active inclusion bodies do not hinder the appropriate folding and formation in native forms of the proteins displayed thereon and also that the active inclusion bodies have the role of immobilizing the displayed proteins in an active form. That is, these results prove that the method of the present invention enables an analysis of the interactions between the proteins while not affecting the real structures and endogenous activities of the binding proteins.

Additionally, as a result of flow cytometry analysis, it was confirmed that the inclusion body cells (PPI+), in which D3E8 (a binding protein where an interaction with the target material (IL6) is present) was displayed), showed a significant increase in the GFP fluorescence by the interaction with the target material, i.e., IL6 protein which was introduced into cells by a process of increasing cell permeability (solid red line), and also a distinct difference in fluorescence compared with that of InVLR5c, which is a binding protein having no affinity for IL6 (solid grey line) (PPI−:PPI+=1× $10^1$:5.5×$10^3$), 450-fold due to the presence of an interaction between proteins (a signal-to-noise ratio), thus confirming that the method of the present invention can clearly determine the presence of interactions between proteins (B of FIG. 13). Additionally, as a result of the analysis on the interactions between proteins according to the affinity for binding proteins, it was confirmed that the intensity of the fluorescence conjugated to a target material increased along with the increase in the affinity of binding proteins, thus confirming that the method of the present invention is a method for analyzing the interactions between proteins enabling a quantitative analysis (C of FIG. 13).

Additionally, as a result of SDS-PAGE analysis of the interaction between proteins (D and E of FIG. 13), it was confirmed that the band of a target material can be confirmed only in the presence of an interaction between a target material and a binding protein. In particular, the molar ratio between the binding protein and the target protein interacting therewith was calculated and confirmed to be 1.0:0.47 (binding protein:target protein) and this suggests that about 40% or more of the active binding proteins are displayed on the inclusion bodies.

The above results support that the method of the present invention enables the isolation and recovery of inclusion bodies cell on an individual cell unit according to the affinity and interactions between the binding proteins displayed on the inclusion bodies and the target materials using a fluorescence microscope as well as using a flow cytometer based on the fluorescence intensity of the target materials. Additionally, since the present invention can determine the presence of an interaction according to the intensity of fluorescence conjugated to the target materials introduced from the outside, the difference in the signal-to-noise ratio becomes a very clear advantage.

Example 16: Library Screening Using an Intracellular Particle Display Technique It was confirmed that a library screening can be performed using the intracellular particle display technique developed in the present invention. The inclusion body cells, in which D3E8 (Kd=2 nM) and F11 (Kd=117 nM) proteins (i.e., binding proteins having an affinity for IL6, a target material) were displayed, respectively, and the inclusion body cells, in which InVLR5c (PPI-) protein (an LRR protein having no affinity for IL6) was displayed, were mixed in a 1:10:10000 ratio to manipulate a library-like environment, and 10,000 E. coli cells having high binding affinity for IL6 were sorted from the samples, which underwent the optimized process of increasing cell permeability by the method of Example 5 and proteins interactions were induced therein, using a flow cytometer (FACSaria). Plasmids were isolated from the sorted cells and then transformed into E. coli DH5a cells. The colonies formed as a result were subjected to PCR amplification and the gene recovery in the cells recovered based on the phenotype (D3E8(F11)-mRFP-CBD protein) was confirmed. The PCR amplification was performed by mixing the primer 12 (SEQ ID NO: 12), primer 13 (SEQ ID NO: 13), and primer 14 (SEQ ID NO: 14) shown in Table 1, and the recovery of the cells in which interactions exist was confirmed based on the size of the amplified genes.

As a result, it was confirmed that a single screening can show about 30,000-fold screening efficiency considering the initial mixing ratio (1/1000) (FIG. 14). The result supports that the present invention can selectively classify only the inclusion body cells in which interactions between proteins exist using a high-throughput device, the flow cytometer (FACS), from a cell library of interaction trapper cells, in which the binding proteins were displayed on active inclusion bodies, and the present invention can provide a library screening system which can effectively recover the genes encoding the interaction proteins in the selectively classified cells.

Based on the above result, a real library was constructed using the repebody, which was used as a model binding protein, and screening work searching for the protein binders for various kinds of targets was performed using the library (FIGS. 15A to 15C). After increasing the cell permeability of the expression library prepared in Example 8, various kinds of targets (mGFP-IL6, sfGFP, fluorescein, and dextran-FITC), to which GFP was bound were treated with the cell library of interaction trapper cells to induce interactions, and the cells of the parts having increased signals (the presence of interactions) in FACS were sorted (FIG. 15A). Only the repebody gene part of the sorted cells was subjected to PCR and the library genes were substituted and inserted into the position of the InVLR5c gene of pInVLR5c-mRFP-CBD to obtain plasmids which were linked to the mRFP-CBD gene. The plasmids were introduced into E. coli BL21 (DE3) by electroporation to obtain transformants, and the sequence of the repebody gene was confirmed by sequencing after random selection of each of the colonies. As a result, various kinds of protein binders that can bind to each of the targets were easily obtained by performing only two repeated screenings at most (D3: SEQ ID NO: 22, F3: SEQ ID NO: 23, I11: SEQ ID NO: 24, I12: SEQ ID NO: 25, I13: SEQ ID NO: 26, M1: SEQ ID NO: 27, M3: SEQ ID NO: 28, M5: SEQ ID NO: 29, M9: SEQ ID NO: 30, DF3: SEQ ID NO: 31, DF6: SEQ ID NO: 32, and DF12: SEQ ID NO: 33). In particular, in the case of a library screening targeting sfGFP, it was possible to selectively recover only the binding protein cells with a desired binding affinity for the targets in the FACS analysis. From the above results, it was proved that the intracellular particle display technique is a library-screening system that enables rapid and easy obtaining of protein binders formed by protein interactions.

Example 17: Screening for Affinity-Maturation Using an Intracellular Particle Display Technique It was confirmed that affinity of binding proteins can be matured using the intracellular particle display technique developed in the present invention. After increasing the permeability of inclusion body cells, on which the binding protein having an affinity for sfGFP (i.e., a target material) was displayed followed by sfGPF treatment, the fluorescence value of the inclusion body cells was measured in an experimental group, in which a purified H2 binding protein was treated as a competitor, and in another experimental group, in which a purified H2 binding protein was not treated as a competitor, using a cytometer (a of FIG. 19). As a result, it was confirmed that the fluorescence value was decreased at least 4-fold in the experimental group treated with a competitor compared to the experimental group not treated with a competitor. Based on the result, a library for affinity maturation was constructed by the intracellular particle display technique using a H2 protein (SEQ ID NO: 34) which binds to sfGFP (FIG. 20). Specifically, the library was constructed by introducing a mutation on the binding domain of the module 2 and 5 in the H2 binding protein (the concave X positions of FIG. 15b) (H2C1: SEQ ID NO: 35, H2C11: SEQ ID NO: 36, H2C1C2: SEQ ID NO: 37, and H2C13: SEQ ID NO: 38).

Using the library along with the addition of a H2 repebody as a competitor, a binding protein with matured affinity, i.e., H2C1 (Kd=518 nM), was selected by competitive screening (b of FIG. 19 and FIGS. 20 and 21). Furthermore, as a result of competitive screening by treating a H2C1 protein as a competitor to the same library, H2C13 (Kd=17.3 nM), which is a binding protein with a 159-fold increase of affinity maturation compared to that of the existing H2 proteins, was successfully isolated (FIGS. 20 and 21). With respect to the affinity maturation screening, binding proteins with increased affinity were easily obtained by performing only two repeated screenings at most, and the interaction between the H2C13 protein and sfGFP was confirmed by their crystal structures (FIGS. 22 and 23).

Example 18: Analysis of Interactions Between Proteins Using an Unpurified Protein It was confirmed by a flow cytometer that the interaction between proteins with different affinity can be distinctively shown even when an unpurified target protein-containing solution (a supernatant of cells crushed by ultrasonication) was used according to the intracellular particle display technique developed in the present invention (FIG. 24).

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method for analyzing the interaction between a binding protein and a target material, comprising:
   providing a cell, which comprises a construct comprising a polynucleotide encoding a fusion protein consisting of the binding protein and an active inclusion body protein;
   expressing the fusion protein in the cell, thereby forming an interaction trapper (IT) cell, wherein the binding protein is displayed on an inclusion body in the IT cell;
   introducing a fluorescence material-conjugated target material into the IT cell by increasing permeability of the cell membrane or the cell wall through cracking, wherein the cracking comprises
   (i) freezing the IT cell;
   (ii) thawing the frozen cell; and
   (iii) adding citric acid to the thawed cell at pH 4-6; and
   measuring the interaction between the binding protein and the target material which is introduced from the outside of the cell, based on the fluorescence intensity of the fluorescence material conjugated to the target material.

2. The method according to claim 1, further comprising introducing the target material into the cell without affecting the activity of the binding protein displayed on the inclusion body and genetic information of the binding protein.

3. The method according to claim 1, wherein the target material is a protein, a nucleic acid, or a chemical compound.

4. The method according to claim 1, wherein the fusion protein further comprises a fluorescent protein.

5. The method according to claim 4, wherein the fluorescent protein and the fluorescence material conjugated to the target material have different wavelengths.

6. The method according to claim 1, wherein the active inclusion body protein is a cellulose-binding domain (CBD) protein.

7. The method according to claim 4, wherein the fluorescent protein is selected from the group consisting of green fluorescent protein (GFP), enhanced green fluorescent protein (EGFP), modified green fluorescent protein (mGFP), red fluorescent protein (RFP), monomeric red fluorescent protein (mRFP), enhanced red fluorescent protein (ERFP), discosoma sp. red (DsRed) fluorescent protein, blue fluorescent protein (BFP), enhanced blue fluorescent protein (EBFP), cyan fluorescent protein (CFP), cyan green fluorescent protein (CGFP), enhanced cyan fluorescent protein (ECFP), yellow fluorescent protein (YFP), enhanced yellow fluorescent protein (EYFP), azami green (AzG), *Heteractis crispa* red fluorescent protein (HcRed), and blue fluorescent protein (BFP).

8. The method according to claim 1, wherein the fluorescence intensity of the cell is measured using a fluorescence microscope or a flow cytometer.

9. The method according to claim 1, wherein the introducing comprises treating the IT cell with a solution containing a target material.

10. The method according to claim 1, wherein the method further comprises introducing a competitive binding protein into the IT cell.

11. A method for isolating a cell specific to a target material, comprising:
   analyzing the interaction between the binding protein and the target material by the method according to claim 1, and
   isolating the cell specific to a target material.

12. The method according to claim 11, wherein the cell is part of a cell library.

13. A method for isolating a gene encoding a binding protein specific to a target material, comprising:
   isolating the gene encoding the binding protein specific to a target material in the cell isolated by the method according to claim 11.

14. The method according to claim 13, further comprising amplifying the isolated gene encoding the binding protein specific to a target material in the cell.

15. The method according to claim 1, wherein the cell is an animal cell, a plant cell, a yeast cell, or a bacterial cell.

16. The method according to claim 1, wherein the cell is *E. coli*, *Streptomyces*, or *Salmonella typhimurium*.

17. The method according to claim 1, wherein the cell is *E. coli*.

18. The method according to claim 1, wherein the binding protein is leucine-rich-repeat (LRR) protein, and the target material is IL6 protein.

19. The method according to claim 1, wherein the freezing is performed at a temperature of −20° C. or above.

20. The method according to claim 1, wherein
   the binding protein is leucine-rich-repeat (LRR) protein,
   the active inclusion body protein is a cellulose-binding domain (CBD) protein, and
   the target material is IL6 protein.

21. The method according to claim 1, wherein the (iii) adding comprises adding citric acid to the thawed cell at pH 4.

22. A method for analyzing the interaction between a binding protein and a target material, comprising:
   transforming a cell with a construct comprising a polynucleotide encoding a fusion protein consisting of the binding protein and an active inclusion body protein;
   expressing the fusion protein in the cell, thereby forming an interaction trapper (IT) cell, wherein the binding protein is displayed on an inclusion body in the IT cell;
   after the transforming, cracking the IT cell in presence of a fluorescence material-conjugated target material, the cracking comprising;
   (i) freezing the IT cell;
   (ii) thawing the frozen cell; and
   (iii) adding an acidic solution or chelating agent to the thawed cell; and
   measuring the interaction between the binding protein and the target material which is introduced from the outside of the cell, based on the fluorescence intensity of the fluorescence material conjugated to the target material,
   wherein the only transformation in the method is the transforming of the cell with said construct.

23. The method according to claim 22, wherein the (iii) adding comprises adding citric acid to the thawed cell at pH 4-6.

24. The method according to claim 22, wherein the (iii) adding comprises adding chelating agent.

25. The method according to claim 22, wherein the binding protein is leucine-rich-repeat (LRR) protein, and the target material is IL6 protein.

* * * * *

```
                            SEQUENCE LISTING

<160> NUMBER OF SEQ ID NOS: 38

<210> SEQ ID NO 1
<211> LENGTH: 78
<212> TYPE: DNA
<213> ORGANISM: artificial
<220> FEATURE:
<223> OTHER INFORMATION: ndeI histag VLR F

<400> SEQUENCE: 1
ggaattccat atgggcagca gccaccacca ccaccaccac agcagcggcg gatccgaaac      60
cattaccgtg agcacccc                                                   78

<210> SEQ ID NO 2
<211> LENGTH: 46
<212> TYPE: DNA
<213> ORGANISM: artificial
<220> FEATURE:
<223> OTHER INFORMATION: gs linker D3E8 R

<400> SEQUENCE: 2
ggacccagag ccgctaccgg taccggtcgg gcaaataatg ctacgc                     46

<210> SEQ ID NO 3
<211> LENGTH: 37
<212> TYPE: DNA
<213> ORGANISM: artificial
<220> FEATURE:
<223> OTHER INFORMATION: gs linker mRFP F

<400> SEQUENCE: 3
ggtagcggct ctgggtccat ggcctcctcc gaggacg                               37

<210> SEQ ID NO 4
<211> LENGTH: 54
<212> TYPE: DNA
<213> ORGANISM: artificial
<220> FEATURE:
<223> OTHER INFORMATION: pt linker mRFP R

<400> SEQUENCE: 4
tcggagggaa ttcaccggaa ccgcgtggca ccagaccggc gccggtggag tggc            54

<210> SEQ ID NO 5
<211> LENGTH: 51
<212> TYPE: DNA
<213> ORGANISM: artificial
<220> FEATURE:
<223> OTHER INFORMATION: pt linker cex F

<400> SEQUENCE: 5
ttccggtgaa ttccctccga cgccgacccc gactagtggt ccggccgggt g               51

<210> SEQ ID NO 6
<211> LENGTH: 32
<212> TYPE: DNA
<213> ORGANISM: artificial
<220> FEATURE:
<223> OTHER INFORMATION: HindIII CBD R

<400> SEQUENCE: 6
```

```
cccccccaagc ttttagccga ccgtgcaggg cg                                   32
```

<210> SEQ ID NO 7
<211> LENGTH: 49
<212> TYPE: DNA
<213> ORGANISM: artificial
<220> FEATURE:
<223> OTHER INFORMATION: gs linker InVLR5c R

<400> SEQUENCE: 7

```
ggacccagag ccgctaccgg taccaacttc cagggtcgga cagataatg                 49
```

<210> SEQ ID NO 8
<211> LENGTH: 76
<212> TYPE: DNA
<213> ORGANISM: artificial
<220> FEATURE:
<223> OTHER INFORMATION: ndeI histag mGFP F

<400> SEQUENCE: 8

```
ggaattccat atgggcagca gccaccacca ccaccaccac agcagcggcg gatccgtgag     60
caagggcgag gagctg                                                     76
```

<210> SEQ ID NO 9
<211> LENGTH: 41
<212> TYPE: DNA
<213> ORGANISM: artificial
<220> FEATURE:
<223> OTHER INFORMATION: gs linker mGFP R

<400> SEQUENCE: 9

```
ggacccagag ccgctaccct tgtacagctc gtccatgccg a                         41
```

<210> SEQ ID NO 10
<211> LENGTH: 46
<212> TYPE: DNA
<213> ORGANISM: artificial
<220> FEATURE:
<223> OTHER INFORMATION: gs linker IL6 F

<400> SEQUENCE: 10

```
ggtagcggct ctgggtccga attcgcccca gtaccccag agaag                      46
```

<210> SEQ ID NO 11
<211> LENGTH: 37
<212> TYPE: DNA
<213> ORGANISM: artificial
<220> FEATURE:
<223> OTHER INFORMATION: HindIII IL6 R

<400> SEQUENCE: 11

```
cccccccaagc ttttacattt gccgaagagc cctcagg                             37
```

<210> SEQ ID NO 12
<211> LENGTH: 20
<212> TYPE: DNA
<213> ORGANISM: artificial
<220> FEATURE:
<223> OTHER INFORMATION: D3E8 specific F

<400> SEQUENCE: 12

```
gcagctgtgg gcgaatcaac                                                 20
```

<210> SEQ ID NO 13
<211> LENGTH: 22

```
<212> TYPE: DNA
<213> ORGANISM: artificial
<220> FEATURE:
<223> OTHER INFORMATION: InVLR5c specific F

<400> SEQUENCE: 13
gacgtatctg attctgaccg gt                                            22

<210> SEQ ID NO 14
<211> LENGTH: 22
<212> TYPE: DNA
<213> ORGANISM: artificial
<220> FEATURE:
<223> OTHER INFORMATION: mRFP R

<400> SEQUENCE: 14
gaagcgcatg aactccttga tg                                            22

<210> SEQ ID NO 15
<211> LENGTH: 108
<212> TYPE: PRT
<213> ORGANISM: Cellulomonas fimi KCTC 9143

<400> SEQUENCE: 15
```

Ser Gly Pro Ala Gly Cys Gln Val Leu Trp Gly Val Asn Gln Trp Asn
1               5                   10                  15

Thr Gly Phe Thr Ala Asn Val Thr Val Lys Asn Thr Ser Ser Ala Pro
            20                  25                  30

Val Asp Gly Trp Thr Leu Thr Phe Ser Phe Pro Ser Gly Gln Gln Val
        35                  40                  45

Thr Gln Ala Trp Ser Ser Thr Val Thr Gln Ser Gly Ser Ala Val Thr
    50                  55                  60

Val Arg Asn Ala Pro Trp Asn Gly Ser Ile Pro Ala Gly Gly Thr Ala
65                  70                  75                  80

Gln Phe Gly Phe Asn Gly Ser His Thr Gly Thr Asn Ala Ala Pro Thr
                85                  90                  95

Ala Phe Ser Leu Asn Gly Thr Pro Cys Thr Val Gly
            100                 105

```
<210> SEQ ID NO 16
<211> LENGTH: 238
<212> TYPE: PRT
<213> ORGANISM: artificial
<220> FEATURE:
<223> OTHER INFORMATION: modified green fluorescent protein

<400> SEQUENCE: 16
```

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val

```
            100                 105                 110
Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 17
<211> LENGTH: 224
<212> TYPE: PRT
<213> ORGANISM: artificial
<220> FEATURE:
<223> OTHER INFORMATION: monomeric red fluorescent protein 1

<400> SEQUENCE: 17

Ala Ser Ser Glu Asp Val Ile Lys Glu Phe Met Arg Phe Lys Val Arg
1               5                   10                  15

Met Glu Gly Ser Val Asn Gly His Glu Phe Glu Ile Glu Gly Glu Gly
            20                  25                  30

Glu Gly Arg Pro Tyr Glu Gly Thr Gln Thr Ala Lys Leu Lys Val Thr
        35                  40                  45

Lys Gly Gly Pro Leu Pro Phe Ala Trp Asp Ile Leu Ser Pro Gln Phe
    50                  55                  60

Gln Tyr Gly Ser Lys Ala Tyr Val Lys His Pro Ala Asp Ile Pro Asp
65                  70                  75                  80

Tyr Leu Lys Leu Ser Phe Pro Glu Gly Phe Lys Trp Glu Arg Val Met
                85                  90                  95

Asn Phe Glu Asp Gly Gly Val Val Thr Val Thr Gln Asp Ser Ser Leu
            100                 105                 110

Gln Asp Gly Glu Phe Ile Tyr Lys Val Lys Leu Arg Gly Thr Asn Phe
        115                 120                 125

Pro Ser Asp Gly Pro Val Met Gln Lys Lys Thr Met Gly Trp Glu Ala
    130                 135                 140

Ser Thr Glu Arg Met Tyr Pro Glu Asp Gly Ala Leu Lys Gly Glu Ile
145                 150                 155                 160

Lys Met Arg Leu Lys Leu Lys Asp Gly Gly His Tyr Asp Ala Glu Val
                165                 170                 175

Lys Thr Thr Tyr Met Ala Lys Lys Pro Val Gln Leu Pro Gly Ala Tyr
            180                 185                 190

Lys Thr Asp Ile Lys Leu Asp Ile Thr Ser His Asn Glu Asp Tyr Thr
        195                 200                 205

Ile Val Glu Gln Tyr Glu Arg Ala Glu Gly Arg His Ser Thr Gly Ala
    210                 215                 220
```

<210> SEQ ID NO 18
<211> LENGTH: 269
<212> TYPE: PRT
<213> ORGANISM: artificial
<220> FEATURE:
<223> OTHER INFORMATION: In-VLR5c

<400> SEQUENCE: 18

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
            260                 265
```

<210> SEQ ID NO 19
<211> LENGTH: 266
<212> TYPE: PRT
<213> ORGANISM: artificial
<220> FEATURE:
<223> OTHER INFORMATION: In-VLR5c-D3E8

<400> SEQUENCE: 19

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45
```

```
Asn Asn Ser Asp Ile Lys Ser Val Gln Gly Ile Gln Tyr Leu Pro Asn
     50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Thr Leu Glu Pro Asn Gln
                     85                  90                  95

Leu Gln Ser Leu Pro Asn Gly Val Phe Asp Lys Leu Thr Asn Leu Lys
                100                 105                 110

Glu Leu Gln Leu Trp Ala Asn Gln Leu Gln Ser Leu Pro Asp Gly Val
            115                 120                 125

Phe Asp Lys Leu Thr Asn Leu Thr Tyr Leu Asn Leu Ala Phe Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Lys Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
                260                 265

<210> SEQ ID NO 20
<211> LENGTH: 266
<212> TYPE: PRT
<213> ORGANISM: artificial
<220> FEATURE:
<223> OTHER INFORMATION: In-VLR5c-F11

<400> SEQUENCE: 20

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
                 20                  25                  30

Asp Ala Val Thr Gln Asn Glu Leu Asn Ser Ile Asp Gln Ile Ile Ala
             35                  40                  45

Asn Asn Ser Asp Ile Lys Ser Val Gln Gly Ile Gln Tyr Leu Pro Asn
     50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Thr Leu Glu Pro Asn Gln
                     85                  90                  95

Leu Gln Ser Leu Pro Asn Gly Val Phe Asp Lys Leu Thr Asn Leu Lys
                100                 105                 110

Glu Leu Ser Leu Trp Met Asn Gln Leu Gln Ser Leu Pro Asp Gly Val
            115                 120                 125

Phe Asp Lys Leu Thr Asn Leu Thr Tyr Leu Asn Leu Ala His Asn Gln
130                 135                 140
```

```
Leu Gln Ser Leu Pro Lys Gly Val Phe Asp Lys Leu Thr Asn Leu Thr
            145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 21
<211> LENGTH: 185
<212> TYPE: PRT
<213> ORGANISM: Homo sapiens

<400> SEQUENCE: 21

Ala Pro Val Pro Pro Gly Glu Asp Ser Lys Asp Val Ala Ala Pro His
1               5                   10                  15

Arg Gln Pro Leu Thr Ser Ser Glu Arg Ile Asp Lys Gln Ile Arg Tyr
            20                  25                  30

Ile Leu Asp Gly Ile Ser Ala Leu Arg Lys Glu Thr Cys Asn Lys Ser
        35                  40                  45

Asn Met Cys Glu Ser Ser Lys Glu Ala Leu Ala Glu Asn Asn Leu Asn
    50                  55                  60

Leu Pro Lys Met Ala Glu Lys Asp Gly Cys Phe Gln Ser Gly Phe Asn
65                  70                  75                  80

Glu Glu Thr Cys Leu Val Lys Ile Ile Thr Gly Leu Leu Glu Phe Glu
                85                  90                  95

Val Tyr Leu Glu Tyr Leu Gln Asn Arg Phe Glu Ser Ser Glu Glu Gln
            100                 105                 110

Ala Arg Ala Val Gln Met Ser Thr Lys Val Leu Ile Gln Phe Leu Gln
        115                 120                 125

Lys Lys Ala Lys Asn Leu Asp Ala Ile Thr Thr Pro Asp Pro Thr Thr
130                 135                 140

Asn Ala Ser Leu Leu Thr Lys Leu Gln Ala Gln Asn Gln Trp Leu Gln
145                 150                 155                 160

Asp Met Thr Thr His Leu Ile Leu Arg Ser Phe Lys Glu Phe Leu Gln
                165                 170                 175

Ser Ser Leu Arg Ala Leu Arg Gln Met
            180                 185

<210> SEQ ID NO 22
<211> LENGTH: 269
<212> TYPE: PRT
<213> ORGANISM: artificial
<220> FEATURE:
<223> OTHER INFORMATION: D3

<400> SEQUENCE: 22

Glu Thr Ile Thr Val Ser Thr Pro Ile Lys Gln Ile Phe Pro Asp Asp
```

```
          1               5                   10                  15
        Ala Phe Ala Glu Thr Ile Lys Ala Asn Leu Lys Lys Lys Ser Val Thr
                        20                  25                  30

Asp Ala Val Thr Gln Asn Glu Leu Asn Ser Ile Asp Gln Ile Ile Ala
                        35                  40                  45

Asn Asn Ser Asp Ile Lys Ser Val Gln Gly Ile Gln Tyr Leu Pro Asn
                    50                  55                  60

Val Arg Tyr Leu Ala Leu Gly Gly Asn Lys Leu His Asp Ile Ser Ala
        65                  70                  75                  80

Leu Lys Glu Leu Thr Asn Leu Thr Tyr Leu Thr Leu Glu Pro Asn Gln
                            85                  90                  95

Leu Gln Ser Leu Pro Asn Gly Val Phe Asp Lys Leu Thr Asn Leu Lys
                        100                 105                 110

Glu Leu Gln Leu Trp Ala Asn Gln Leu Gln Ser Leu Pro Asp Gly Val
                        115                 120                 125

Phe Asp Lys Leu Thr Asn Leu Thr Tyr Leu Asn Leu Ala His Asn Gln
                    130                 135                 140

Leu Gln Ser Leu Pro Lys Gly Val Phe Asp Lys Leu Thr Asn Leu Thr
        145                 150                 155                 160

Glu Leu Asp Leu Ser Tyr Asn Gln Leu Gln Ser Leu Pro Glu Gly Val
                            165                 170                 175

Phe Asp Lys Leu Thr Gln Leu Lys Asp Leu Arg Leu Tyr Gln Asn Gln
                        180                 185                 190

Leu Lys Ser Val Pro Asp Gly Val Phe Asp Arg Leu Thr Ser Leu Gln
                        195                 200                 205

Tyr Ile Trp Leu His Asp Asn Pro Trp Asp Cys Thr Cys Pro Gly Ile
                    210                 215                 220

Arg Tyr Leu Ser Glu Trp Ile Asn Lys His Ser Gly Val Val Arg Asn
        225                 230                 235                 240

Ser Ala Gly Ser Val Ala Pro Asp Ser Ala Lys Cys Ser Gly Ser Gly
                            245                 250                 255

Lys Pro Val Arg Ser Ile Ile Cys Pro Thr Leu Glu Val
                        260                 265

<210> SEQ ID NO 23
<211> LENGTH: 269
<212> TYPE: PRT
<213> ORGANISM: artificial
<220> FEATURE:
<223> OTHER INFORMATION: F3

<400> SEQUENCE: 23

Glu Thr Ile Thr Val Ser Thr Pro Ile Lys Gln Ile Phe Pro Asp Asp
        1               5                   10                  15

Ala Phe Ala Glu Thr Ile Lys Ala Asn Leu Lys Lys Lys Ser Val Thr
                        20                  25                  30

Asp Ala Val Thr Gln Asn Glu Leu Asn Ser Ile Asp Gln Ile Ile Ala
                    35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
        65                  70                  75                  80

Leu Lys Glu Leu Thr Asn Leu Thr Tyr Leu Arg Leu Pro Ile Asn Gln
                            85                  90                  95

Leu Gln Ser Leu Pro Asn Gly Val Phe Asp Lys Leu Thr Asn Leu Lys
```

```
            100                 105                 110
Glu Leu Ser Leu Trp Arg Asn Gln Leu Gln Ser Leu Pro Asp Gly Val
        115                 120                 125

Phe Asp Lys Leu Thr Asn Leu Thr Tyr Leu Asn Leu Ala His Asn Gln
        130                 135             140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
            165                 170                 175

Phe Asp Lys Leu Thr Gln Leu Lys Asp Leu Arg Leu Tyr Gln Asn Gln
        180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr Leu Glu Val
        260                 265

<210> SEQ ID NO 24
<211> LENGTH: 269
<212> TYPE: PRT
<213> ORGANISM: artificial
<220> FEATURE:
<223> OTHER INFORMATION: I11

<400> SEQUENCE: 24

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Leu Leu Met Ile Asn Gln
                85                  90                  95

Leu Gln Ser Leu Pro Asn Gly Val Phe Asp Lys Leu Thr Asn Leu Lys
            100                 105                 110

Glu Leu Gly Leu Gly Pro Asn Gln Leu Gln Ser Leu Pro Asp Gly Val
        115                 120                 125

Phe Asp Lys Leu Thr Asn Leu Thr Tyr Leu Asn Leu Ala His Asn Gln
        130                 135             140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
            165                 170                 175

Phe Asp Lys Leu Thr Gln Leu Lys Asp Leu Arg Leu Tyr Gln Asn Gln
        180                 185                 190

Leu Lys Ser Val Pro Asp Gly Val Phe Asp Arg Leu Thr Ser Leu Gln
```

```
                195                 200                 205
Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
                260                 265

<210> SEQ ID NO 25
<211> LENGTH: 269
<212> TYPE: PRT
<213> ORGANISM: artificial
<220> FEATURE:
<223> OTHER INFORMATION: I12

<400> SEQUENCE: 25

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Lys Leu Pro Leu Asn Gln
                85                  90                  95

Leu Gln Ser Leu Pro Asn Gly Val Phe Asp Lys Leu Thr Asn Leu Lys
            100                 105                 110

Glu Leu Asp Leu Arg Pro Asn Gln Leu Gln Ser Leu Pro Asp Gly Val
        115                 120                 125

Phe Asp Lys Leu Thr Asn Leu Thr Tyr Leu Asn Leu Ala His Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
                260                 265

<210> SEQ ID NO 26
<211> LENGTH: 269
<212> TYPE: PRT
```

<213> ORGANISM: artificial
<220> FEATURE:
<223> OTHER INFORMATION: I13

<400> SEQUENCE: 26

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65              70                  75                  80

Leu Lys Glu Leu Thr Asn Leu Thr Tyr Leu Leu Pro Arg Asn Gln
            85                  90                  95

Leu Gln Ser Leu Pro Asn Gly Val Phe Asp Lys Leu Thr Asn Leu Lys
            100                 105                 110

Glu Leu Pro Leu Pro His Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr Leu Glu Val
            260                 265
```

<210> SEQ ID NO 27
<211> LENGTH: 269
<212> TYPE: PRT
<213> ORGANISM: artificial
<220> FEATURE:
<223> OTHER INFORMATION: M1

<400> SEQUENCE: 27

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60
```

```
Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Ile Leu Thr Gly Asn Gln
                 85                  90                  95

Leu Gln Ser Leu Pro Asn Gly Val Phe Asp Lys Leu Thr Asn Leu Lys
            100                 105                 110

Glu Leu Ala Leu Ala Cys Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
            260                 265

<210> SEQ ID NO 28
<211> LENGTH: 269
<212> TYPE: PRT
<213> ORGANISM: artificial
<220> FEATURE:
<223> OTHER INFORMATION: M3

<400> SEQUENCE: 28

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
 50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Ile Leu Thr Gly Asn Gln
                 85                  90                  95

Leu Gln Ser Leu Pro Asn Gly Val Phe Asp Lys Leu Thr Asn Leu Lys
            100                 105                 110

Glu Leu Ala Leu Gly Cys Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160
```

-continued

```
Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
                260                 265
```

<210> SEQ ID NO 29
<211> LENGTH: 269
<212> TYPE: PRT
<213> ORGANISM: artificial
<220> FEATURE:
<223> OTHER INFORMATION: M5

<400> SEQUENCE: 29

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Gly Leu Ala Ala Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255
```

```
Lys Pro Val Arg Ser Ile Ile Cys Pro Thr Leu Glu Val
        260                 265
```

<210> SEQ ID NO 30
<211> LENGTH: 269
<212> TYPE: PRT
<213> ORGANISM: artificial
<220> FEATURE:
<223> OTHER INFORMATION: M9

<400> SEQUENCE: 30

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Phe Leu Gly Ala Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
            260                 265
```

<210> SEQ ID NO 31
<211> LENGTH: 269
<212> TYPE: PRT
<213> ORGANISM: artificial
<220> FEATURE:
<223> OTHER INFORMATION: DF3

<400> SEQUENCE: 31

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30
```

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
 50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Arg Leu Arg Arg Asn Gln
                85                  90                  95

Leu Gln Ser Leu Pro Asn Gly Val Phe Asp Lys Leu Thr Asn Leu Lys
                100                 105                 110

Glu Leu Gly Leu Gly Asn Gln Leu Gln Ser Leu Pro Asp Gly Val
                115                 120                 125

Phe Asp Lys Leu Thr Asn Leu Thr Tyr Leu Asn Leu Ala His Asn Gln
            130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
                260                 265

<210> SEQ ID NO 32
<211> LENGTH: 269
<212> TYPE: PRT
<213> ORGANISM: artificial
<220> FEATURE:
<223> OTHER INFORMATION: DF6

<400> SEQUENCE: 32

Glu Thr Ile Thr Val Ser Thr Pro Ile Lys Gln Ile Phe Pro Asp Asp
 1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
 50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Leu Leu Ser Asn Gln
                85                  90                  95

Leu Gln Ser Leu Pro Asn Gly Val Phe Asp Lys Leu Thr Asn Leu Lys
                100                 105                 110

Glu Leu Glu Leu Asp Ala Asn Gln Leu Gln Ser Leu Pro Asp Gly Val
                115                 120                 125

```
Phe Asp Lys Leu Thr Asn Leu Thr Tyr Leu Asn Leu Ala His Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
                210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
                260                 265
```

<210> SEQ ID NO 33
<211> LENGTH: 269
<212> TYPE: PRT
<213> ORGANISM: artificial
<220> FEATURE:
<223> OTHER INFORMATION: DF12

<400> SEQUENCE: 33

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Arg Leu Arg Arg Asn Gln
                85                  90                  95

Leu Gln Ser Leu Pro Asn Gly Val Phe Asp Lys Leu Thr Asn Leu Lys
                100                 105                 110

Glu Leu Gly Leu Ser Val Asn Gln Leu Gln Ser Leu Pro Asp Gly Val
            115                 120                 125

Phe Asp Lys Leu Thr Asn Leu Thr Tyr Leu Asn Leu Ala His Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
                210                 215                 220
```

```
Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
                260                 265
```

<210> SEQ ID NO 34
<211> LENGTH: 269
<212> TYPE: PRT
<213> ORGANISM: artificial
<220> FEATURE:
<223> OTHER INFORMATION: H2

<400> SEQUENCE: 34

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu His Leu Leu Asn Gln
                85                  90                  95

Leu Gln Ser Leu Pro Asn Gly Val Phe Asp Lys Leu Thr Asn Leu Lys
                100                 105                 110

Glu Leu Lys Leu Thr Glu Asn Gln Leu Gln Ser Leu Pro Asp Gly Val
            115                 120                 125

Phe Asp Lys Leu Thr Asn Leu Thr Tyr Leu Asn Leu Ala His Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
                260                 265
```

<210> SEQ ID NO 35
<211> LENGTH: 269
<212> TYPE: PRT
<213> ORGANISM: artificial
<220> FEATURE:
<223> OTHER INFORMATION: H2C1

```
<400> SEQUENCE: 35

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30

Asp Ala Val Thr Gln Asn Glu Leu Asn Ser Ile Asp Gln Ile Ile Ala
                35                  40                  45

Asn Asn Ser Asp Ile Lys Ser Val Gln Gly Ile Gln Tyr Leu Pro Asn
            50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu His Leu Leu Asn Gln
                85                  90                  95

Leu Gln Ser Leu Pro Asn Gly Val Phe Asp Lys Leu Thr Asn Leu Lys
            100                 105                 110

Glu Leu Lys Leu Thr Glu Asn Gln Leu Gln Ser Leu Pro Asp Gly Val
            115                 120                 125

Phe Asp Lys Leu Thr Asn Leu Thr Arg Leu Gln Leu Gln Arg Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr Leu Glu Val
            260                 265

<210> SEQ ID NO 36
<211> LENGTH: 269
<212> TYPE: PRT
<213> ORGANISM: artificial
<220> FEATURE:
<223> OTHER INFORMATION: H2C11

<400> SEQUENCE: 36

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30

Asp Ala Val Thr Gln Asn Glu Leu Asn Ser Ile Asp Gln Ile Ile Ala
                35                  40                  45

Asn Asn Ser Asp Ile Lys Ser Val Gln Gly Ile Gln Tyr Leu Pro Asn
            50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu His Leu Leu Leu Asn Gln
```

```
            85                  90                  95
Leu Gln Ser Leu Pro Asn Gly Val Phe Asp Lys Leu Thr Asn Leu Lys
            100                 105                 110

Glu Leu Lys Leu Thr Glu Asn Gln Leu Gln Ser Leu Pro Asp Gly Val
        115                 120                 125

Phe Asp Lys Leu Thr Asn Leu Thr Ser Leu Glu Leu Ser Tyr Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
            260                 265

<210> SEQ ID NO 37
<211> LENGTH: 269
<212> TYPE: PRT
<213> ORGANISM: artificial
<220> FEATURE:
<223> OTHER INFORMATION: H2C1C2

<400> SEQUENCE: 37

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Ser Leu Ala Leu Ala Ser Asn Lys Leu His Asp Ile Ser Ala
65                  70                  75                  80

Leu Lys Glu Leu Thr Asn Leu Thr Tyr Leu His Leu Leu Asn Gln
            85                  90                  95

Leu Gln Ser Leu Pro Asn Gly Val Phe Asp Lys Leu Thr Asn Leu Lys
            100                 105                 110

Glu Leu Lys Leu Thr Glu Asn Gln Leu Gln Ser Leu Pro Asp Gly Val
        115                 120                 125

Phe Asp Lys Leu Thr Asn Leu Thr Arg Leu Gln Leu Gln Arg Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
```

```
                    180                 185                 190
Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
                260                 265

<210> SEQ ID NO 38
<211> LENGTH: 269
<212> TYPE: PRT
<213> ORGANISM: artificial
<220> FEATURE:
<223> OTHER INFORMATION: H2C13

<400> SEQUENCE: 38

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Met Leu Ala Leu Ala Ser Asn Lys Leu His Asp Ile Ser Ala
65                  70                  75                  80

Leu Lys Glu Leu Thr Asn Leu Thr Tyr Leu His Leu Leu Asn Gln
                85                  90                  95

Leu Gln Ser Leu Pro Asn Gly Val Phe Asp Lys Leu Thr Asn Leu Lys
                100                 105                 110

Glu Leu Lys Leu Thr Glu Asn Gln Leu Gln Ser Leu Pro Asp Gly Val
            115                 120                 125

Phe Asp Lys Leu Thr Asn Leu Thr Arg Leu Gly Leu Gln Cys Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
                260                 265
```